US008420591B2

(12) United States Patent
Kufe

(10) Patent No.: US 8,420,591 B2
(45) Date of Patent: Apr. 16, 2013

(54) MUC1 AND GALECTIN-3

(75) Inventor: Donald W. Kufe, Wellesley, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 692 days.

(21) Appl. No.: 12/517,762

(22) PCT Filed: Dec. 7, 2007

(86) PCT No.: PCT/US2007/086760
§ 371 (c)(1),
(2), (4) Date: Nov. 17, 2009

(87) PCT Pub. No.: WO2008/073817
PCT Pub. Date: Jun. 19, 2008

(65) Prior Publication Data
US 2010/0098683 A1   Apr. 22, 2010

Related U.S. Application Data

(60) Provisional application No. 60/873,847, filed on Dec. 8, 2006.

(51) Int. Cl.
*A61K 38/00* (2006.01)
*A61P 35/00* (2006.01)
*C07K 14/00* (2006.01)

(52) U.S. Cl.
USPC .......... 514/1.1; 514/19.2; 514/19.3; 530/300; 530/324

(58) Field of Classification Search .................. None
See application file for complete search history.

(56) References Cited

U.S. PATENT DOCUMENTS

| | | | |
|---|---|---|---|
| 4,918,166 A | 4/1990 | Kingsman et al. | 530/350 |
| 7,247,297 B2 | 7/2007 | Weichselbaum et al. | 424/93.2 |
| 2002/0110841 A1 | 8/2002 | Kufe | 435/7.23 |
| 2003/0105000 A1* | 6/2003 | Pero et al. | 514/12 |
| 2004/0018181 A1 | 1/2004 | Kufe et al. | 424/93.21 |
| 2004/0166543 A1 | 8/2004 | Kufe | 435/7.23 |
| 2004/0197328 A1* | 10/2004 | Young et al. | 424/141.1 |
| 2005/0042209 A1 | 2/2005 | Kufe et al. | 424/93.21 |
| 2005/0053606 A1 | 3/2005 | Kufe et al. | 424/155.1 |
| 2007/0105767 A1 | 5/2007 | Kharbanda et al. | 514/12 |
| 2007/0202134 A1 | 8/2007 | Kufe et al. | 424/277.1 |
| 2008/0090770 A1 | 4/2008 | Belmares et al. | 514/17 |
| 2008/0107661 A1 | 5/2008 | Kufe | 424/172.1 |
| 2008/0286264 A1 | 11/2008 | Kufe | 424/130.1 |
| 2008/0311575 A1 | 12/2008 | Kufe | 435/6 |
| 2009/0087437 A1 | 4/2009 | Kufe | 424/139.1 |
| 2009/0092600 A1 | 4/2009 | Kufe | 424/133.1 |
| 2009/0098054 A1 | 4/2009 | Kufe | 424/9.2 |

FOREIGN PATENT DOCUMENTS
WO   WO 2006/088906   8/2006

OTHER PUBLICATIONS

Bowie et al. (Science, 1990, 257:1306-1310).*
Burgess et al. (J of Cell Bio. 111:2129-2138, 1990).*
Lazar et al. (Molecular and Cellular Biology, 1988, 8:1247-1252).*
Dillman (Annals of Internal Medicine, 1989 111:592-603).*
Zou et al. (Carcinogenesis Nov. 2004 26(2): 309-318).*
Walsh et al. (Breast Cancer Res. Treat. 2000 58:255-266).*
Bitonti and Dumont (Advanced Drug Delivery Rev. Aug. 12, 2006 58:1106-1118).*
Akahani et al., "Galectin-3: a novel antiapoptotic molecule with a functional BHI (NWGR) domain of Bcl-2 family," *Cancer Res.*, 57:5272-5276, 1997.
Aruffo et al., "CD44 is the principal cell surface receptor for hyaluronate," *Cell*, 61:1303-1313, 1990.
Bagga et al., "Regulation by let-7 and lin-4 miRNAs results in target mRNA degradation," *Cell*, 122:553-63, 2005.
Bartel, Cell, "MicroRNAs: genomics, biogenesis, mechanism, and function," 116:281-97, 2004.
Califice et al., "Galectin-3 and cancer (Review)," *Int. J. Oncol.*, 25:983-992, 2004.
Chijiwa et al., "A newly synthesized selective casein kinase I inhibitor, N-(2-aminoethyl)-5-chloroisoquinoline-8-sulfonamide, and affinity purification of casein kinase I from bovine testis," *J. Biol. Chem.*, 264:4924-7, 1989.
Cogni and Masino, "Gene silencing in Neurospora crassa requires a protein homologous to RNA-dependent RNA polymerase," *Nature*, 399:166-169, 1999.
Cogni et al., "Transgene silencing of the al-1 gene in vegetative cells of Neurospora is mediated by a cytoplasmic effector and does not depend on DNA-DNA interactions or DNA methylation," *EMBO J.*, 15:3153-3163, 1996.
Cristiano et al., "Molecular conjugates: a targeted gene delivery vector for molecular medicine," *J. Mol. Med.*, 73:479-486, 1995.
Dudas et al., "Expression of human intestinal mucin is modulated by the beta-galactoside binding protein galectin-3 in colon cancer," *Gastroenterology*, 123:817-826, 2002.
Duraisamy et al., "Distinct evolution of the human carcinoma-associated transmembrane mucins, MUC1, MUC4 and MUC16," *Gene*, 373:28-34, 2006.
Fire et al., "Potent and specific genetic interference by double-stranded RNA in Caenorhabditis elegans," *Nature*, 391:806-811, 1998.
Gendler et al., "A highly immunogenic region of a human polymorphic epithelial mucin expressed by carcinomas is made up of tandem repeats," *J. Biol. Chem.*, 263:12820-12823, 1988.
Huang et al., "MUC1 cytoplasmic domain coactivates Wnt target gene transcription and confers transformation," *Cancer Biol. Ther.*, 2(6):702-6, 2003.
Huang et al., "MUC1 oncoprotein blocks glycogen synthase kinase 3beta-mediated phosphorylation and degradation of beta-catenin," *Cancer Res.*, 65(22):10413-22, 2005.

(Continued)

*Primary Examiner* — Peter J Reddig
(74) *Attorney, Agent, or Firm* — Parker Highlander PLLC

(57) ABSTRACT

The invention provides methods of identifying and making compounds that inhibit the interaction between MUC1 and galectin-3. Also embraced by the invention are in vivo and in vitro methods of inhibiting such an interaction and of inhibiting the expression of galectin-3 by a cell.

2 Claims, 19 Drawing Sheets

OTHER PUBLICATIONS

Hudson et al., "High avidity scFv multimers; diabodies and triabodies," *J. Immunol. Methods*, 231(1-2):177-189, 1999.

Hughes, "Secretion of the galectin family of mammalian carbohydrate-binding proteins," *Biochim. Biophys. Acta.*, 1473:172-185, 1999.

Huston et al., "Engineered antibodies take center stage," *Hum. Antibodies*, 10(3-4):127-142, 2001.

Johnson et al., "RAS is regulated by the let-7 microRNA family," *Cell*, 120:635-647, 2005.

Kennerdell and Carthew, "Use of dsRNA-mediated genetic interference to demonstrate that frizzled and frizzled 2 act in the wingless pathway," *Cell*, 95:1017-1026, 1998.

Krutzfeldt et al., "Silencing of microRNAs in vivo with 'antagomirs'," *Nature*, 438:685-9, 2005.

Kufe et al., "Differential reactivity of a novel monoclonal antibody (DF3) with human malignant versus benign breast tumors," *Hybridoma*, 3:223-232, 1984.

Lee and Ambros, "An extensive class of small RNAs in *Caenorhabditis elegans*," *Science*, 294:862-864, 2001.

Levitin et al., "The MUC1 SEA module is a self-cleaving domain," *J. Biol. Chem.*, 280:33374-33386, 2005.

Li and Kufe, "The human DF3/MUC1 carcinoma-associated antigen signals nulcear localization of the catenin P120(ctn)," *Biochem. Biophys. Res. Commun.*, 281(2):440-3, 2001.

Li et al., "DF3/MUC1 signaling in multiple myeloma cells is regulated by interleukin-7," *Cancer Biol. Ther.*, 2(2):187-93, 2003.

Li et al., "Heregulin targets gamma-catenin to the nucleolus by a mechanism dependent on the DF3/MUC1 oncoprotein," *Mol. Cancer Res.*, 1:765-775, 2003.

Li et al., "Human DF3/MUC1 carcinoma-associated protein functions as an oncogene," *Oncogene*, 22:6107-6110, 2003.

Li et al., "Interaction of glycogen synthase kinase 3beta with the DF3/MUC1 carcinoma-associated antigen and beta-catenin," *Mol. Cell. Biol.*, 18:7216-7224, 1998.

Li et al., "Interaction of human MUC1 and beta-catenin is regulated by Lck and ZAP-70 in activated Jurkat T cells," *Biochem. Biophys. Res. Commun.*, 315(2):471-6, 2004.

Li et al., "The c-Src tyrosine kinase regulates signaling of the human DF3/MUC1 carcinoma-associated antigen with GSK3 beta and beta-catenin," *J. Biol. Chem.*, 276(9):6061-4, 2001.

Li et al., "The epidermal growth factor receptor regulates interaction of the human DF3/MUC1 carcinoma antigen with c-Src and beta-catenin," *J. Biol. Chem.*, 276:35239-35242, 2001.

Ligtenberg et al., "Cell-associated episialin is a complex containing two proteins derived from a common precursor," *J. Biol. Chem.*, 267:6171-6177, 1992.

Lim et al., "Microarray analysis shows that some microRNAs downregulate large numbers of target mRNAs," *Nature*, 433:769-73, 2005.

Lin et al., "Galectin-3 enhances cyclin D(1) promoter activity through SP1 and a cAMP-responsive element in human breast epithelial cells," *Oncogene*, 21:8001-8010, 2002.

Liu and Rabinovich, "Galectins as modulators of tumour progression," *Nat. Rev. Cancer*, 5:29-41, 2005.

Macao et al., "Autoproteolysis coupled to protein folding in the SEA domain of the membrane-bound MUC1 mucin," *Nat. Struct. Mol. Biol.*, 13:71-76, 2006.

Mashhoon et al., "Crystal structure of a conformation-selective casein kinase-1 inhibitor," *J. Biol. Chem.*, 275:20052-20060, 2000.

Matarrese et al., "Galectin-3 overexpression protects from cell damage and death by influencing mitochondrial homeostasis," *FEBS Lett.*, 473:311-315, 2000.

Meggio et al., "Ribofuranosyl-benzimidazole derivatives as inhibitors of casein kinase-2 and casein kinase-1," *Eur. J. Biochem.*, 187:89-94, 1990.

Merlo et al., "Frequent alteration of the DF3 tumor-associated antigen gene in primary human breast carcinomas.," *Cancer Res.*, 49:6966-6971, 1989.

Misquitta and Paterson, "Targeted disruption of gene function in *Drosophila* by RNA interference (RNA-i): a role for nautilus in embryonic somatic muscle formation," *Proc. Natl. Acad. Sci. USA*, 96:1451-1456, 1999.

Nangia-Makker et al., "Induction of tumorigenicity by galectin-3 in a non-tumorigenic human breast carcinoma cell line," *Int. J. Oncol.*, 7:1079-1087, 1995.

Ochieng, "Extracellular functions of galectin-3," *Glycoconj. J.*, 19:527-535, 2004.

Paron et al., "Nuclear localization of Galectin-3 in transformed thyroid cells: a role in transcriptional regulation," *Biochem. Biophys. Res. Commun.*, 302:545-553, 2003.

Partridge et al., *Science*, "Regulation of cytokine receptors by Golgi N-glycan processing and endocytosis," 306:120-124, 2004.

Patrone et al., "Nuclear run-on assay using biotin labeling, magnetic bead capture and analysis by fluorescence-based RT-PCR," *Biotechniques*, 29(5):1012-1014, 1016-1017, 2000.

Patterson et al., "Understanding the biochemical activities of galectin-1 and galectin-3 in the nucleus.," *Glycoconj J.*, 19:499-506, 2004.

PCT International Preliminary Report on Patentability, issued in International Application No. PCT/US2007/086760, mailed Jun. 18, 2009.

Poljak, "Production and structure of diabodies," *Structure*, 2:12:1121-1123, 1994.

Raina et al., "MUC1 oncoprotein blocks nulcear trageting of c-Abl in the apopototic response to DNA damage," *EMBO J.*, 25(16):3774-83, 2006.

Raina et al., "The MUC1 oncoprotein activates the anti-apoptotic phosphoinositide 3-kinease/Akt and Bcl-xL pathways in rat 3Y1 fibroblasts," *J. Biol. Chem.*, 279(20):20607-12, 2004.

Ramasamy et al., "The MUC1 and galectin-3 oncoproteins function in a microRNA-dependent regulatory loop," *Molecular Cell.*, 27:992-1004, 2007.

Ren et al., "Human MUC1 carcinoma-associated protein confers resistance to gentoxic anticancer agents," *Cancer Cell*, 5(2):163-75, 2004.

Ren et al., "MUC1 oncoprotein functions in activation of fibroblast growth factor receptor signaling," *Mol. Cancer Res.*, 4(11):873-83, 2006.

Ren et al., "MUC1 oncoprotein is targeted to mitochondria by heregulin-induced activation of c-Src and the molecular chaperone HSP90," *Oncogoene*, 25(1):20-31, 2006.

Rena et al., "D4476, a cell-permeant inhibitor of CK1, suppresses the site-specific phosphorylation and nuclear exclusion of FOXO1a,"*EMBO Rep.*, 5:60-65, 2004.

Romano and Masino, "Quelling: transient inactivation of gene expression in *Neurospora crassa* by transformation with homologous sequences," *Mol. Microbiol.*, 6:3343-3353, 1992.

Schroeder et al., "MUC1 overexpression results in mammary gland tumorigenesis and prolonged alveolar differentiation," *Oncogene*, 23:5739-5747, 2004.

Seetharaman et al., "X-ray crystal structure of the human galectin-3 carbohydrate recognition domain at 2.1-A resolution,". *J. Biol. Chem.*, 273:13047-13052, 1998.

Shimura et al., "Galectin-3, a novel binding partner of beta-catenin," *Cancer Res.*, 64:6363-6367, 2004.

Siddiqui et al., "Isolation and sequencing of a cDNA coding for the human DF3 breast carcinoma-associated antigen," *Proc. Natl. Acad. Sci. USA*, 85:2320-2323, 1988.

Stocks et al., "Intrabodies: production and promise," *Drug. Discov. Today*, 9(22):960-966, 2004.

Takenaka et al., "Galectin-3 and metastasis," *Glycoconj. J.*, 19:543-549, 2004.

Takenaka et al., "Malignant transformation of thyroid follicular cells by galectin-3," *Cancer Lett.*, 195:111-119, 2003.

Takenaka et al., "Nuclear export of phosphorylated galectin-3 regulates its antiapoptotic activity in response to chemotherapeutic drugs," *Mol. Cell Biol.*, 24:4395-4406, 2004.

Van de Brule et al., "Expression of galectins in cancer: a critical review," *Glycoconj.*, 239:537-542, 2004.

Walzel et al., "Galectin-induced activation of the transcription factors NFAT and AP-1 in human Jurkat T-lymphocytes," *Cell Signal*, 14:861-868, 2002.

Wei et al., "Human MUC1 oncoportein regulates p53-responsive gene transcription in the genotoxic stress response," *Cancer Cell*, 7(2):167-78, 2005.

Wei et al., "MUC1 oncoprotein stabilizes and activates estrogen receptor alpha," *Mol. Cell.*, 21(2):295-305, 2006.

Wen et al., "Nuclear Association of the Cytoplasmic Tail of MUC1 and β-Catenin," *J. Biol. Chem.*, 278:38026-38039, 2003.

Wheeler et al., "Intrabody and intrakine strategies for molecular therapy.," *Mol. Ther.*, 8(3):355-366, 2003.

Wu and Belasco, "Micro-RNA regulation of the mammalian lin-28 gene during neuronal differentiation of embryonal carcinoma cells.," *Mol. Cell. Biol.*, 25:9198-9208, 2005.

Wu et al., "MicroRNAs direct rapid deadenylation of mRNA," *Proc. Natl. Acad. Sci. USA*, 103:4034-9, 2006.

Yamamoto et al., "Interaction of the DF3/MUC1 breast carcinoma-associated antigen and beta-catenin in cell adhesion.," *J. Biol. Chem.*, 272:12492-12494, 1997.

Yoshii et al., "Galectin-3 phosphorylation is required for its anti-apoptotic function and cell cycle arrest," *J. Biol. Chem.*, 277:6852-6857, 2002.

Yu et al., "Galectin-3 interaction with Thomsen-Friedenreich disaccharide on cancer-associated MUC1 causes increased cancer cell endothelial adhesion," *Journal of Biological Chemistry*, 282(1): 773-781, 2007.

Yu et al., "Galectin-3 enhances epithelial cancer cell adhesion to endothelial cells by interaction with cancer-associated MUC1," *Gastroenterology*, 128(4-2): A186, 2005.

Yu et al., "Galectin-3 translocates to the perinuclear membranes and inhibits cytochrome c release from the mitochondria. A role for synexin in galectin-3 translocation," *J. Biol. Chem.*, 277:15819-15827, 2002.

* cited by examiner

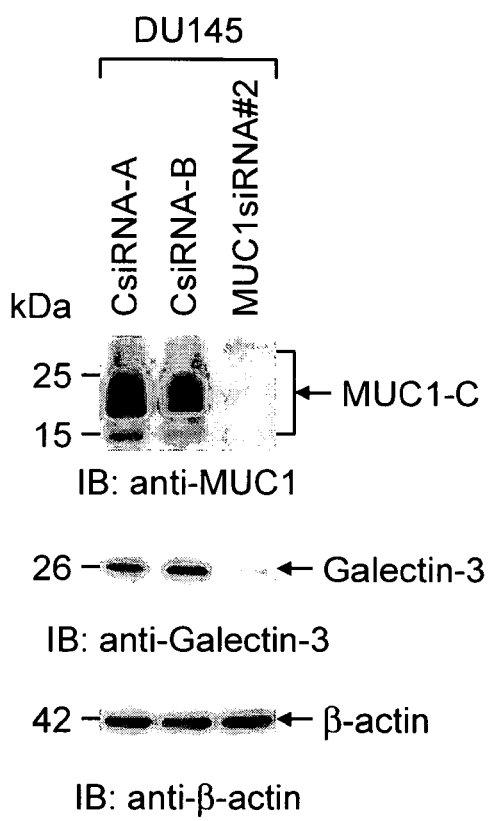
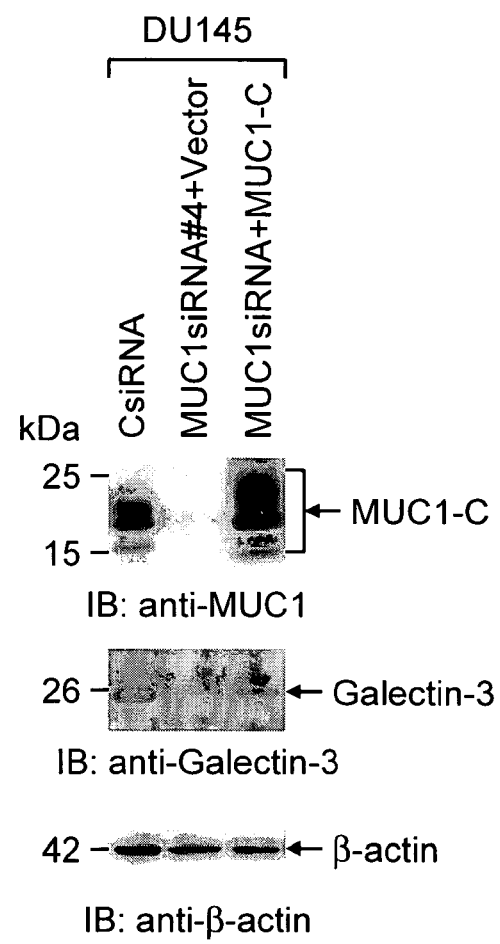
FIG. 1D
FIG. 1E

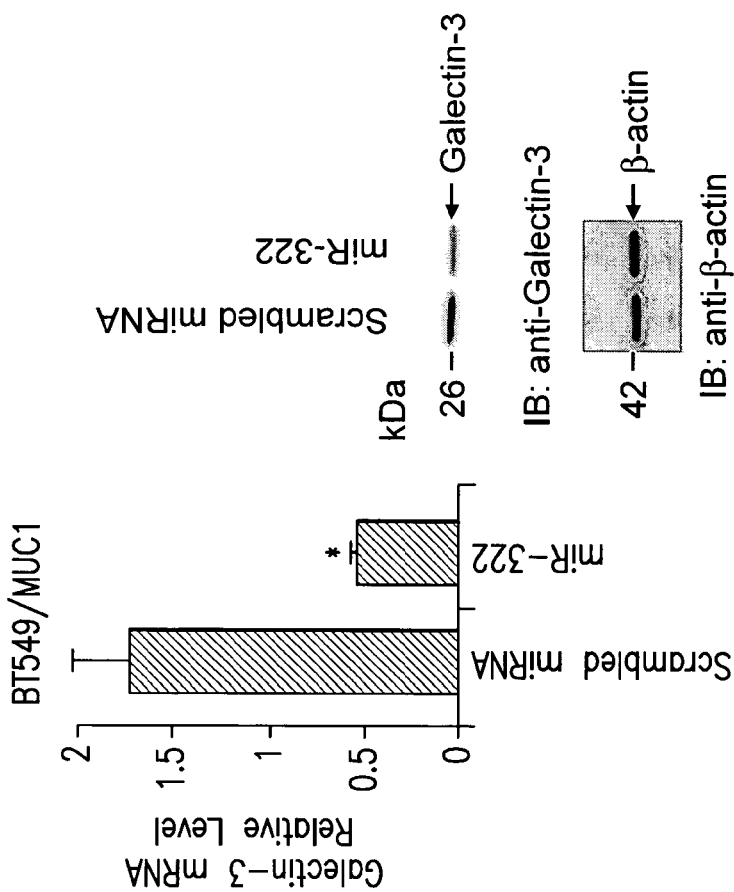
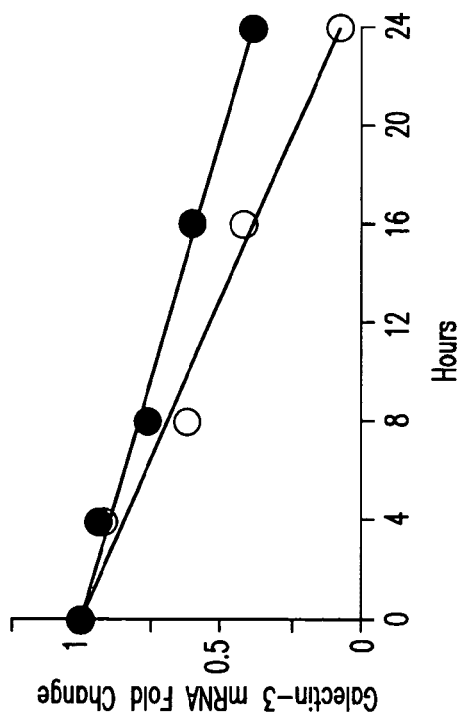
FIG. 3E
FIG. 3D

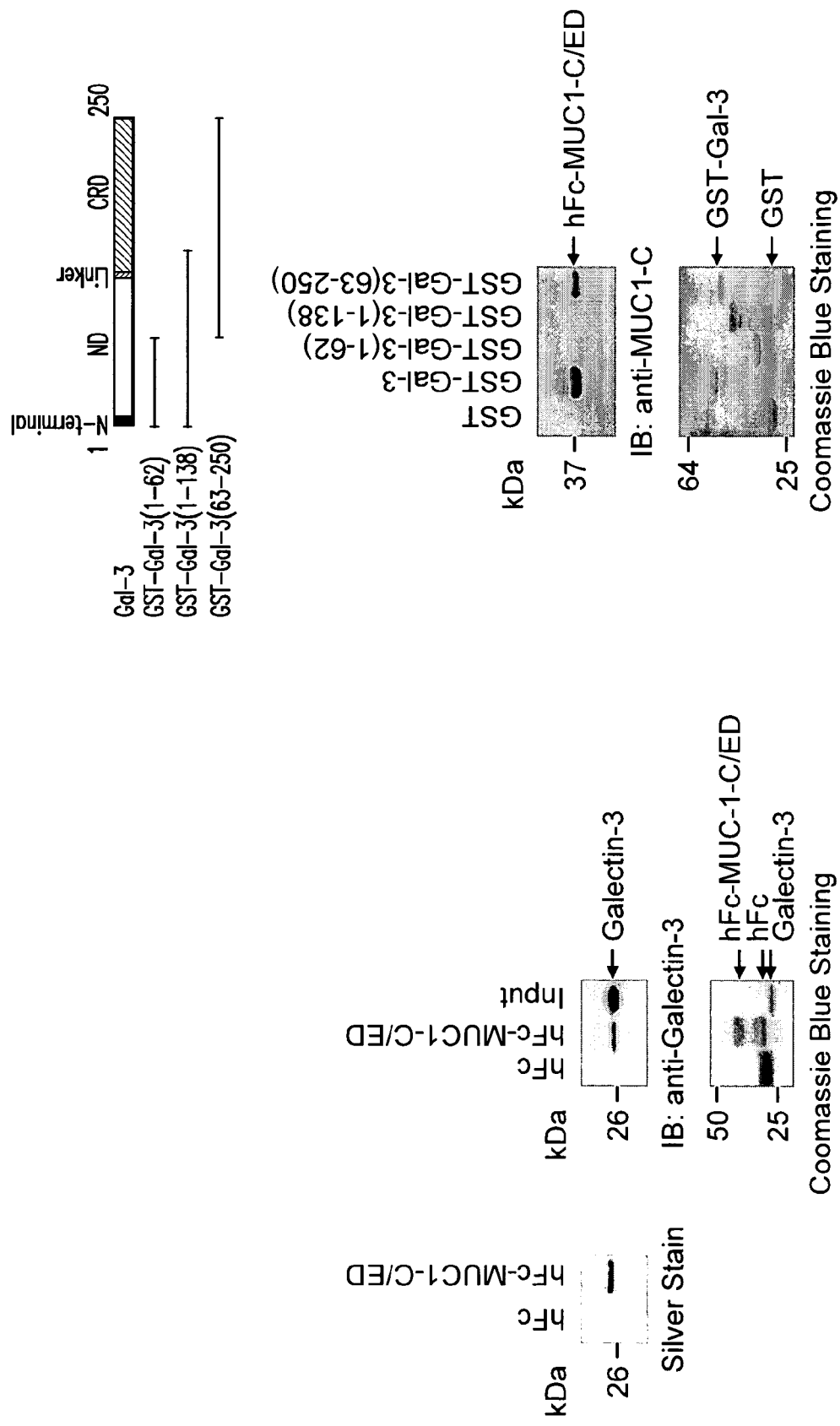

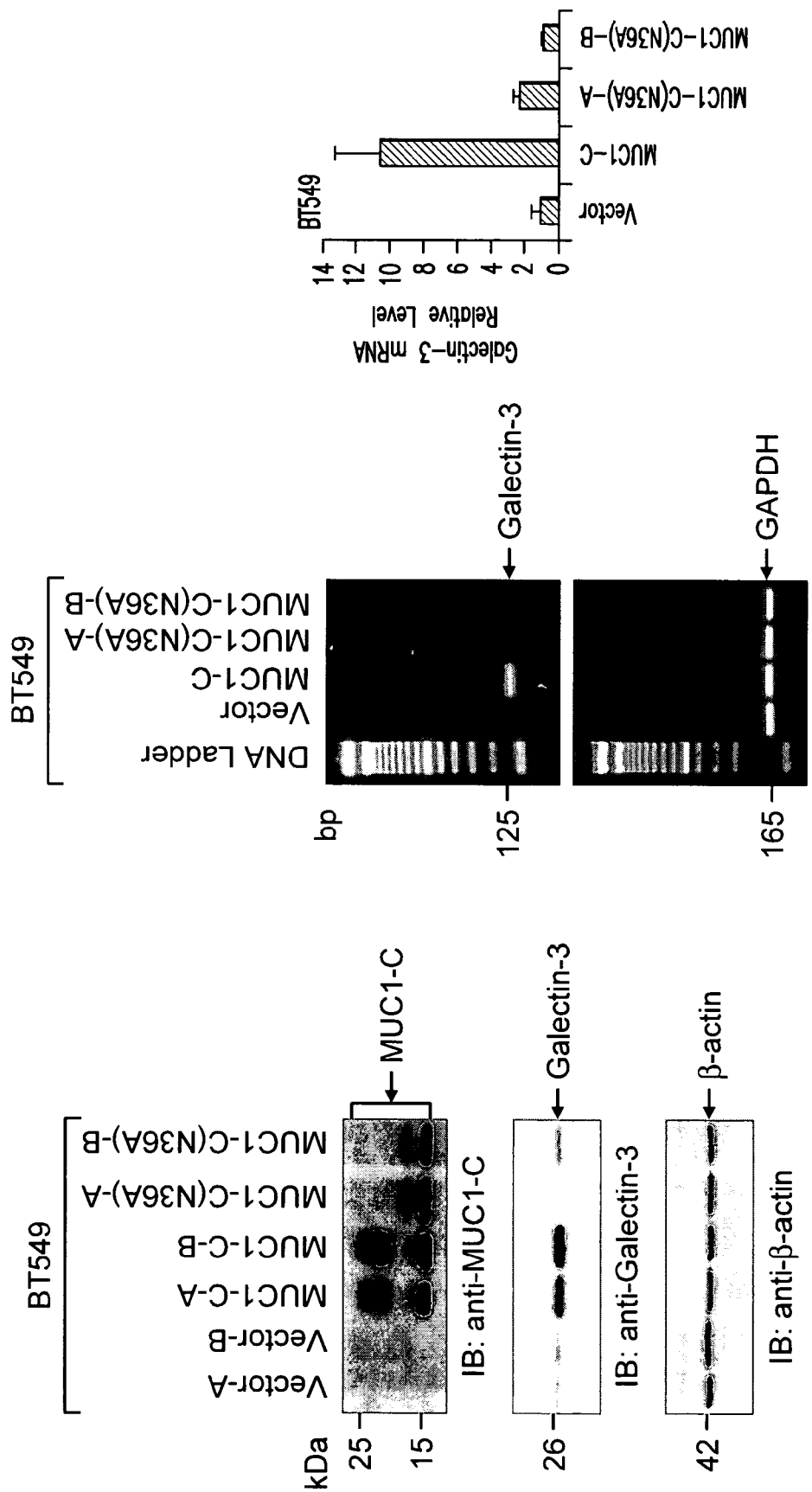

SEQUENCE LISTING

```
<160> NUMBER OF SEQ ID NOS: 25

<210> SEQ ID NO 1
<211> LENGTH: 158
<212> TYPE: PRT
<213> ORGANISM: Artificial Sequence
<220> FEATURE:
<223> OTHER INFORMATION: Synthetic peptide

<400> SEQUENCE: 1

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr Asn Leu Thr Ile Ser Asp Val Ser Val Ser Asp Val Pro
        35                  40                  45

Phe Pro Phe Ser Ala Gln Ser Gly Ala Gly Val Pro Gly Trp Gly Ile
    50                  55                  60

Ala Leu Leu Val Leu Val Cys Val Leu Val Ala Leu Ala Ile Val Tyr
65                  70                  75                  80

Leu Ile Ala Leu Ala Val Cys Gln Cys Arg Arg Lys Asn Tyr Gly Gln
                85                  90                  95

Leu Asp Ile Phe Pro Ala Arg Asp Thr Tyr His Pro Met Ser Glu Tyr
            100                 105                 110

Pro Thr Tyr His Thr His Gly Arg Tyr Val Pro Pro Ser Ser Thr Asp
            115                 120                 125
```

```
Arg Ser Pro Tyr Glu Lys Val Ser Ala Gly Asn Gly Gly Ser Ser Leu
130                 135                 140
Ser Tyr Thr Asn Pro Ala Val Ala Thr Ser Ala Asn Leu
145                 150                 155

<210> SEQ ID NO 2
<211> LENGTH: 250
<212> TYPE: PRT
<213> ORGANISM: Artificial Sequence
<220> FEATURE:
<223> OTHER INFORMATION: Synthetic peptide

<400> SEQUENCE: 2

Met Ala Asp Asn Phe Ser Leu His Asp Ala Leu Ser Gly Ser Gly Asn
1               5                   10                  15
Pro Asn Pro Gln Gly Trp Pro Gly Ala Trp Gly Asn Gln Pro Ala Gly
            20                  25                  30
Ala Gly Gly Tyr Pro Gly Ala Ser Tyr Pro Gly Ala Tyr Pro Gly Gln
        35                  40                  45
Ala Pro Pro Gly Ala Tyr Pro Gly Gln Ala Pro Pro Gly Ala Tyr His
    50                  55                  60
Gly Ala Pro Gly Ala Tyr Pro Gly Ala Pro Ala Pro Gly Val Tyr Pro
65                  70                  75                  80
Gly Pro Pro Ser Gly Pro Gly Ala Tyr Pro Ser Ser Gly Gln Pro Ser
                85                  90                  95
Ala Pro Gly Ala Tyr Pro Ala Thr Gly Pro Tyr Gly Ala Pro Ala Gly
            100                 105                 110
Pro Leu Ile Val Pro Tyr Asn Leu Pro Leu Pro Gly Gly Val Val Pro
        115                 120                 125
Arg Met Leu Ile Thr Ile Leu Gly Thr Val Lys Pro Asn Ala Asn Arg
    130                 135                 140
Ile Ala Leu Asp Phe Gln Arg Gly Asn Asp Val Ala Phe His Phe Asn
145                 150                 155                 160
Pro Arg Phe Asn Glu Asn Asn Arg Arg Val Ile Val Cys Asn Thr Lys
                165                 170                 175
Leu Asp Asn Asn Trp Gly Arg Glu Glu Arg Gln Ser Val Phe Pro Phe
            180                 185                 190
Glu Ser Gly Lys Pro Phe Lys Ile Gln Val Leu Val Glu Pro Asp His
        195                 200                 205
Phe Lys Val Ala Val Asn Asp Ala His Leu Leu Gln Tyr Asn His Arg
    210                 215                 220
Val Lys Lys Leu Asn Glu Ile Ser Lys Leu Gly Ile Ser Gly Asp Ile
225                 230                 235                 240
Asp Leu Thr Ser Ala Ser Tyr Thr Met Ile
                245                 250

<210> SEQ ID NO 3
<211> LENGTH: 21
<212> TYPE: PRT
<213> ORGANISM: Artificial Sequence
<220> FEATURE:
<223> OTHER INFORMATION: Synthetic Primer

<400> SEQUENCE: 3

Ala Ala Gly Gly Thr Ala Cys Cys Ala Thr Ala Ala Thr Gly Thr
1               5                   10                  15
Cys Cys Ala Cys Gly
            20
```

<210> SEQ ID NO 4
<211> LENGTH: 20
<212> TYPE: RNA
<213> ORGANISM: Artificial Sequence
<220> FEATURE:
<223> OTHER INFORMATION: Synthetic primer

<400> SEQUENCE: 4
aaacgugagg cgcugcuaua                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aagttcagtg ccagctctac                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
cgcttaccga ttcagaatgg                                               20

<210> SEQ ID NO 7
<211> LENGTH: 20
<212> TYPE: RNA
<213> ORGANISM: Artificial Sequence
<220> FEATURE:
<223> OTHER INFORMATION: Synthetic primer

<400> SEQUENCE: 7
aaacgugagg cgcugcuaua                                               20

<210> SEQ ID NO 8
<211> LENGTH: 21
<212> TYPE: RNA
<213> ORGANISM: Artificial Sequence
<220> FEATURE:
<223> OTHER INFORMATION: Synthetic primer

<400> SEQUENCE: 8
gucaggucaa acggccuaga u                                             21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
aagttcagtg cccagctcta c                                             21

<210> SEQ ID NO 10
<211> LENGTH: 21
<212> TYPE: RNA
<213> ORGANISM: Artificial Sequence
<220> FEATURE:
<223> OTHER INFORMATION: Synthetic primer

```
<400> SEQUENCE: 10
guucagugcc cagcucuacu u                                           21

<210> SEQ ID NO 11
<211> LENGTH: 19
<212> TYPE: RNA
<213> ORGANISM: Artificial Sequence
<220> FEATURE:
<223> OTHER INFORMATION: Synthetic primer

<400> SEQUENCE: 11
guucagugcc cagcucuac                                              19

<210> SEQ ID NO 12
<211> LENGTH: 21
<212> TYPE: RNA
<213> ORGANISM: Artificial Sequence
<220> FEATURE:
<223> OTHER INFORMATION: Synthetic primer

<400> SEQUENCE: 12
guagagcugg gcacugaacu u                                           21

<210> SEQ ID NO 13
<211> LENGTH: 19
<212> TYPE: RNA
<213> ORGANISM: Artificial Sequence
<220> FEATURE:
<223> OTHER INFORMATION: Synthetic primer

<400> SEQUENCE: 13
guagagcugg gcacugaac                                              19

<210> SEQ ID NO 14
<211> LENGTH: 19
<212> TYPE: RNA
<213> ORGANISM: Artificial Sequence
<220> FEATURE:
<223> OTHER INFORMATION: Synthetic primer

<400> SEQUENCE: 14
gguaccauca auguccacg                                              19

<210> SEQ ID NO 15
<211> LENGTH: 19
<212> TYPE: RNA
<213> ORGANISM: Artificial Sequence
<220> FEATURE:
<223> OTHER INFORMATION: Synthetic primer

<400> SEQUENCE: 15
cguggacauu gaugguacc                                              19

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
caaccagtac ttgtattttg aatg                                        24

<210> SEQ ID NO 17
<211> LENGTH: 23
<212> TYPE: DNA
```

```
<213> ORGANISM: Artificial Sequence
<220> FEATURE:
<223> OTHER INFORMATION: Synthetic primer

<400> SEQUENCE: 17
caatgagaac aacaggagag tca                                           23

<210> SEQ ID NO 18
<211> LENGTH: 16
<212> TYPE: DNA
<213> ORGANISM: Artificial Sequence
<220> FEATURE:
<223> OTHER INFORMATION: Synthetic primer

<400> SEQUENCE: 18
gcagcgcctc acgttt                                                   16

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
gcgtgtcatc cttgcgcag                                                19

<210> SEQ ID NO 20
<211> LENGTH: 24
<212> TYPE: RNA
<213> ORGANISM: Artificial Sequence
<220> FEATURE:
<223> OTHER INFORMATION: Synthetic primer

<400> SEQUENCE: 20
gguauagcag cgccucacgu uuug                                          24

<210> SEQ ID NO 21
<211> LENGTH: 24
<212> TYPE: RNA
<213> ORGANISM: Artificial Sequence
<220> FEATURE:
<223> OTHER INFORMATION: Synthetic primer

<400> SEQUENCE: 21
cacggaucua ggucguaacg uagg                                          24

<210> SEQ ID NO 22
<211> LENGTH: 98
<212> TYPE: RNA
<213> ORGANISM: Artificial Sequence
<220> FEATURE:
<223> OTHER INFORMATION: Synthetic primer

<400> SEQUENCE: 22 cgagggauia cagcagcaau ucauguuuug aaguguucua aauggumcaa aacgugaggc   60
gcugcuauac ccccucgugg ggaagguaga agugggg                            98

<210> SEQ ID NO 23
<211> LENGTH: 22
<212> TYPE: RNA
<213> ORGANISM: Artificial Sequence
<220> FEATURE:
<223> OTHER INFORMATION: Synthetic primer

<400> SEQUENCE: 23
```

```
cauguguaaa gguuucaugu uc                                              22

<210> SEQ ID NO 24
<211> LENGTH: 20
<212> TYPE: RNA
<213> ORGANISM: Artificial Sequence
<220> FEATURE:
<223> OTHER INFORMATION: Synthetic primer

<400> SEQUENCE: 24
auaucgucgc ggagugcaaa                                                 20

<210> SEQ ID NO 25
<211> LENGTH: 58
<212> TYPE: PRT
<213> ORGANISM: Artificial Sequence
<220> FEATURE:
<223> OTHER INFORMATION: Synthetic peptide

<400> SEQUENCE: 25

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr Asn Leu Thr Ile Ser Asp Val Ser Val Ser Asp Val Pro
        35                  40                  45

Phe Pro Phe Ser Ala Gln Ser Gly Ala Gly
    50                  55
```

MUC1 AND GALECTIN-3

This application is a national phase application under 35 U.S.C. §371 of International Application No. PCT/US2007/086760 filed Dec. 7, 2007, which claims the benefit of U.S. Provisional Application No. 60/873,847 filed Dec. 8, 2006. The entire contents of these applications are incorporated by reference.

The government owns rights in the invention pursuant to grant CA97098 from the National Cancer Institute of the National Institutes of Health.

1. FIELD OF THE INVENTION

This invention relates to regulation of cell growth, and more particularly to the regulation of cancer cell growth.

2. DESCRIPTION OF RELATED ART

The MUC1 protein is overexpressed by greater than 800,000 of the 1.4 million tumors diagnosed in the United States each year.

Galectins are a family of lectins that contain conserved carbohydrate-recognition domains (CRDs) of about 130 amino acids with specificity for β-galactosides found on both N- and O-linked glycans (Liu and Rabinovich, 2005). Of the 15 known mammalian galectins, the widely expressed galectin-3 is a structurally unique member with an N-terminal domain (ND) of repetitive sequences rich in proline, glycine and tyrosine residues upstream to the CRD. The ND lacks a carbohydrate-binding function, but is essential for the biologic activity of galectin-3 (Seetharaman et al., 1998).

Galectin-3 overexpression has been found to be associated with the development of human malignancies (Liu and Rabinovich (2005; van den Brule et al. (2004); Califice et al. (2004). Cytosolic galectin-3 is targeted to the plasma membrane and released into the extracellular space where it functions in the regulation of cell migration and adhesion (Ochieng et al., 2004). Galectin-3 is also targeted to the nucleus, where it is involved in regulating pre-mRNA splicing (Patterson et al., 2004) and activation of certain transcription factors (Lin et al., 2002; Walzel et al., 2002). As found with MUC1 (Huang et al., 2005), galectin-3 binds directly to β-catenin and induces the transcriptional activity of Tcf-4 (Shimura et al., 2004).

Like MUC1 (Ren et al., 2004; Wei et al., 2005), galectin-3 blocks the apoptotic response of breast cancer cells to genotoxic anti-cancer agents (Takenaka et al., 2004a). The anti-apoptotic activity of galectin-3 is regulated by casein kinase 1-mediated phosphorylation of nuclear galectin-3 on Ser-6 (Yoshii et al., 2002) and thereby its export to the cytoplasm (Takenaka et al., 2004b). Translocation of galectin-3 to mitochondria is associated with inhibition of cytochrome c release which contributes to protection against the induction of apoptosis (Matarrese et al., 2000; Yu et al., 2002). Galectin-3 also contains an Asn-Trp-Gly-Arg (NWGR) motif that is conserved in the BH1 domain of the Bcl-2 family members. This motif is of importance to the galectin-3 anti-apoptotic function (Akahani et al., 1997). Little is known about the regulation of galectin-3 expression in cancer cells.

SUMMARY OF THE INVENTION

The inventors have found that MUC1-C is N-glycosylated, binds to galectin-3, and induces galectin-3 expression by a post-transcriptional mechanism. This application demonstrates that MUC1 and galectin-3 function as part of a regulatory loop in which (i) N-glycosylation of MUC1-C is necessary for suppression of miR-322 and thereby upregulation of galectin-3, and (ii) binding of galectin-3 to N-glycosylated MUC1 is of functional importance to integration of MUC1 with the epidermal growth factor receptor (EGFR) signaling pathway.

The invention includes methods for identifying compounds useful for inhibiting the interaction between MUC1-C and galectin-3. Such compounds can be useful for directly promoting apoptosis of MUC1-expressing cancer cells, for enhancing the efficacy of genotoxic chemotherapeutic agents against such cancer cells, and as anti-cancer prophylactic agents. Also included in the invention are methods of inhibiting the interaction between galectin-3 and MUC1 in which cells (e.g., carcinoma cells such as breast carcinoma cells) are contacted with compounds that inhibit the interaction between MUC1 and galectin-3. While the experiments described herein were generally performed with human MUC1, galectin-3, and cells, it is understood that the methods described herein can be performed with corresponding molecules from any of the mammalian species recited below.

More specifically, the invention provides methods of identifying compounds that inhibit binding of MUC1-C to galectin-3. The methods include: (a) providing a MUC1-C test agent; (b) providing a galectin-3 test agent that binds to the MUC1-C test agent; (c) contacting the MUC1-C test agent with the galectin-3 test agent in the presence of a test compound under conditions that permit the binding of the MUC1-C test agent with the galectin-3 test agent in absence of the test compound; and (d) determining whether the test compound inhibits binding of the MUC1-C test agent to the galectin-3 test agent. The contacting can be carried out in a cell-free system, in a cell, or on the surface of a cell. In some embodiments, the MUC1-C test agent comprises a peptide fragment of MUC1-C (e.g., all or part of the extracellular domain of MUC1-C N-glycosylated at residue N36). In some embodiments, the MUC1-C test agent is a polypeptide (e.g., a soluble polypeptide) comprising a peptide fragment of the extracellular domain of MUC1-C fused to an immunoglobulin Fc region.

Also featured are methods of identifying compounds that inhibit activation of galectin-3 expression by MUC1. The methods include (a) providing a cell that expresses MUC1; (b) contacting the cell with a test compound under conditions that permit the expression of galectin-3 in absence of the test compound; and (d) determining whether the test compound inhibits expression of galectin-3. In some embodiments, the cell comprises a nucleic acid sequence comprising a 3' untranslated region of galectin-3 operably linked to a sequence encoding a reporter polypeptide (e.g., an enzyme or fluorescent polypeptide). In some embodiments, the test compound is microRNA-322 (miR-322).

Also featured are methods of generating compounds that inhibit the interaction between MUC1-C and galectin-3. The methods include: (a) providing the three-dimensional structure of a molecule comprising a peptide fragment of galectin-3 or a peptide fragment of MUC1-C; (b) designing, based on the three dimensional structure, a compound comprising a region that inhibits the interaction between MUC1-C and galectin-3; and (c) producing the compound. The methods can further include determining whether the compound generated inhibits the interaction between MUC1-C and galectin-3.

Further, the invention includes processes of manufacturing compounds by performing any of the above methods and, after determining that a compound inhibits the interaction between MUC1-C and galectin-3 or inhibits the activation of galectin-3 expression by MUC1, manufacturing the compound.

Still further, the invention includes compounds (e.g., small molecules, polypeptides, and nucleic acids) identified, generated, or manufactured by the above methods.

In another aspect, the invention features methods of inhibiting binding of MUC1-C to galectin-3 or inhibiting association of MUC1 and EGFR in a cancer cell that expresses MUC1-C by contacting the cancer cell with a compound (e.g., a small molecule, polypeptide, or polynucleotide) that inhibits binding of galectin-3 to the extracellular domain of MUC1-C and/or inhibits activation of galectin-3 expression by MUC1. In some embodiments, the compound includes: a peptide fragment of MUC1-C or galectin-3; a peptide fragment of the extracellular domain of MUC1-C; a peptide fragment of the extracellular domain of MUC1-C fused to an immunoglobulin Fc region; all or part of the carbohydrate binding domain of galectin-3; or all or part of amino acids 63-250 or 117-244 of galectin-3 (SEQ ID NO:2). In some embodiments, the compound is an antibody, or an antibody fragment, that binds to galectin-3 or the extracellular domain of MUC1-C (e.g., the extracellular domain of MUC1-C N-glycosylated at residue N36). In further embodiments, the compound is a β-galactoside carbohydrate (e.g., lactose) or a carbohydrate analog that binds to galectin-3. In further embodiments, the compound is an inhibitor of MUC1-C glycosylation or a compound that reduces the glycosylation of MUC1-C.

In other aspects, the invention includes methods of inhibiting expression of galectin-3 in cancer cells that express MUC1. The methods include (a) identifying a subject as having a cancer comprising a cancer cell that expresses MUC1; and (b) introducing into the cell a compound that inhibits the expression of MUC1. In some embodiments, the compound is a nucleic acid. Exemplary nucleic acids include antisense nucleic acids, small interfering RNAs (siRNAs), and nucleic acids that direct the expression of an antisense nucleic acid or siRNA. In some embodiments, the compound is a nucleic acid that includes a nucleic acid having the sequence of miR-322. In some embodiments, the step of introducing includes administration of the nucleic acid to the cancer cell and uptake of the nucleic acid by the cancer cell. In some embodiments, the step of introducing includes administering to a mammalian subject (e.g., a human subject), and uptake by the cancer cell of, a nucleic acid: (i) from which sense and anti-sense strands of the siRNA can be transcribed under the direction of separate TREs; or (ii) from which both sense and anti-sense strands of the siRNA can be transcribed under the direction of a single TRE.

The cancer cell can be in a mammalian subject (e.g., a human subject). When the cancer cell is in a subject, the contacting can include delivering (e.g., administering) the compound to the subject (e.g., locally or systemically). When the compound is a protein (e.g., a polypeptide or an antibody), the administration can include direct administration or administering to the subject (a) a nucleic acid comprising a nucleotide sequence encoding the protein, the nucleotide sequence being operably linked to a transcriptional regulatory element (TRE) (e.g., a DF3 enhancer) and/or (b) a recombinant cell (e.g., a transfected cell or a progeny of a transfected cell, made by transfecting a cell derived from the subject) that is transfected with the nucleic acid and that secretes the protein. When the compound is a polynucleotide (e.g., a nucleic acid aptamer, an antisense nucleic acid, a small interfering RNA, or a microRNA), the administration can include direct administration or administering to the subject a nucleic acid comprising a nucleotide sequence encoding the polynucleotide operably linked to a transcriptional regulatory element (TRE) (e.g., a DF3 enhancer).

Exemplary cancer cells that can be the target of the methods described herein include cells of a cancer selected from the group consisting of breast cancer, lung cancer, colon cancer, pancreatic cancer, renal cancer, stomach cancer, liver cancer, bone cancer, hematological cancer, neural tissue cancer, melanoma, ovarian cancer, testicular cancer, prostate cancer, cervical cancer, vaginal cancer, and bladder cancer.

Further, the invention includes methods of killing cancer cells by before, after, or at the same time as, performing the above methods, exposing the cells to one or more genotoxic agents, e.g., one or more forms of ionizing radiation or one or more chemotherapeutic agents (e.g., cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verapamil, podophyllotoxin, tamoxifen, taxol, transplatinum, 5-fluorouracil, vincristin, vinblastin, methotrexate, or an analog of any of the aforementioned).

In other aspects, the invention includes methods of inhibiting expression of galectin-3 in cancer cells that expresses MUC1. The methods include (a) identifying a subject as having a cancer comprising a cancer cell that expresses MUC1; and (b) introducing into the cell a nucleic acid that inhibits the expression of MUC1. Exemplary nucleic acids include antisense nucleic acids, small interfering RNAs (siRNAs), and nucleic acids that direct the expression of an antisense nucleic acid or siRNA. In some embodiments, the step of introducing includes administration of the nucleic acid to the cancer cell and uptake of the nucleic acid by the cancer cell. In some embodiments, the step of introducing includes administering to a mammalian subject (e.g., a human subject), and uptake by the cancer cell of, a nucleic acid: (i) from which sense and anti-sense strands of the siRNA can be transcribed under the direction of separate TREs; or (ii) from which both sense and anti-sense strands of the siRNA can be transcribed under the direction of a single TRE.

In further aspects, the invention features methods of promoting apoptosis of a cell (e.g., a cancer cell) that include determining whether the cell expresses MUC1; and if the cell expresses MUC1, contacting the cell with a compound that inhibits phosphorylation of galectin-3 by casein kinase 1.

Other methods featured by the invention are methods of diagnosing a test cell that include measuring the level of galectin-3 or a MUC1-galectin-3 complex in a test cell, wherein an enhanced level of galectin-3 or MUC1-galectin-3 complex in the test cell is an indication that the test cell is a cancer cell.

"Polypeptide" and "protein" are used interchangeably and mean any peptide-linked chain of amino acids, regardless of length or post-translational modification. The MUC1-C and galectin-3 molecules and test agents used in any of the methods of the invention can contain or be wild-type proteins or can be variants that have not more than fifty (e.g., not more than: one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required as that: (i) such variants of MUC1-C have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type MUC1-C to bind to galectin-3; and (ii) such variants of a galectin-3 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type galectin-3 to bind to MUC1-C.

As used herein, a "MUC1-C test agent" contains, or is, (a) full-length, wild-type mature MUC1-C, (b) a part of MUC1-C that is shorter than full-length, wild-type, mature MUC1-C, or (c) (a) or (b) but with one or more (see above) conservative substitutions. "Parts of a MUC1-C" include fragments (e.g., MUC1 C-ter or the extracellular domain (ED) of MUC1-C) as well deletion variants (terminal as well internal deletions) of MUC1-C. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. MUC1-C test agents can include internal or terminal (carboxy or amino) irrelevant amino acid sequences (e.g., sequences derived from other proteins or synthetic sequences not corresponding to any naturally occurring protein). These added irrelevant sequences will generally be about 1-50 (e.g., two, four, eight, ten, 15, 20, 25, 30, 35, 40, or 45) amino acids in length. MUC1-C test agents other than full-length, wild-type, mature MUC1-C will have at least 50% (e.g., at least 50%, at least 60%, at least 70%, at least 80%, at least 90%, at least 95%, at least 98%, at least 99%, at least 99.5%, or 100% or more) of the ability of the full-length, wild-type, mature MUC1-C to bind to galectin-3.

As used herein, a "galectin-3 test agent" contains, or is, (a) full-length, wild-type mature galectin-3, (b) a part of galectin-3 that is shorter than full-length, wild-type, mature galectin-3, or (c) (a) or (b) but with one or more (see above) conservative substitutions. "Parts of a galectin-3" include fragments (e.g., amino acids 63-250 or the carbohydrate binding domain of galectin-3) as well deletion variants (terminal as well internal deletions) of galectin-3. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Galectin-3 test agents can include internal or terminal (carboxy or amino) irrelevant amino acid sequences (e.g., sequences derived from other proteins or synthetic sequences not corresponding to any naturally occurring protein). These added irrelevant sequences will generally be about 1-50 (e.g., two, four, eight, ten, 15, 20, 25, 30, 35, 40, or 45) amino acids in length. Galectin-3 test agents other than full-length, wild-type, mature galectin-3 will have at least 50% (e.g., at least 50%, at least 60%, at least 70%, at least 80%, at least 90%, at least 95%, at least 98%, at least 99%, at least 99.5%, or 100% or more) of the ability of the full-length, wild-type, mature galectin-3 to bind to MUC1-C.

As used herein, "operably linked" means incorporated into a genetic construct so that expression control sequences effectively control expression of a coding sequence of interest.

The use of the term "or" in the claims is used to mean "and/or" unless explicitly indicated to refer to alternatives only or the alternative are mutually exclusive, although the disclosure supports a definition that refers to only alternatives and "and/or." Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A, 1B, 1C, 1D, 1E. MUC1 upregulates galectin-3 expression. 1A—Lysates from the indicated cells were immunoblotted with anti-MUC1-C, anti-galectin-3 and anti-β-actin. 1B—The empty pIRES-puro vector and pIRES-puro-MUC1 were stably transfected into BT549 breast cancer cells. Lysates from the transfectants were immunoblotted with the indicated antibodies. The BT549/MUC1-A and -B cells represent two separately isolated clones. 1C—Lysates from ZR-75-1/vector-A and ZR-75-1/MUC1siRNA#2-A cells were immunoblotted with the indicated antibodies. 1D—Lysates from DU145 prostate cancer cells stably expressing the pRNA-U6.1/Neo CsiRNA or MUC1siRNA#2 were immunoblotted with the indicated antibodies. 1E—DU145 cells stably expressing MUC1siRNA#4 were transfected with pIRES-puro2 or pIRES-puro2-MUC1-C. Lysates were immunoblotted with the indicated antibodies. DU145/CsiRNA cells were included for comparison.

Figure 1A:
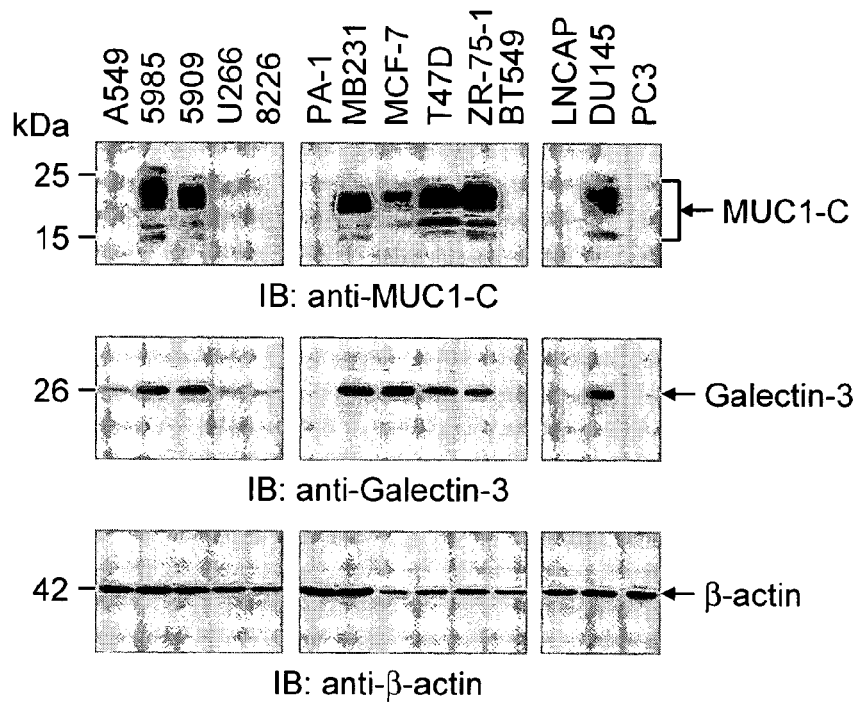

FIGS. 3A, 3B, 3C, 3D, 3E, 3F, 3G. MUC1 downregulates miR-322 and thereby increases stability of galectin-3 mRNA. 3A—Model of the pre-miR stem-loop structure encoding miR-424 and miR-322 (SEQ ID NO:22). 3B—Sequence alignment of human miR-322 with mouse and rat miR-322 and with the galectin-3 3'UTR (SEQ ID NO:23 and SEQ ID NO:24). 3C—Northern blot analyses of RNA from the indicated BT549, ZR-75-1 and DU145 cells probed for miR-322 (upper panels) and U6 snRNA as a loading control (lower panels). 3D—BT549/vector cells were transfected with an antisense 2'-0-methyl oligoribonucleotide targeted against miR-322 or a scrambled 2'-0methyl oligoribonucleotide as a control for 48 h. The cells were treated with actinomycin 0 5 and harvested at the indicated times. Total RNA was analyzed for galectin-3 and GAPDH mRNA levels by quantitative RT-PCR. The results are expressed as relative galectin-3 mRNA levels for BT549 cells transfected with the scrambled oligo (0) or the anti-miR-322 (D). 3E—BT549IMUC1 cells were transfected with a pre-miR-322 or a scrambled miRNA and selected in the presence of blasticidin. Cells were assayed for galectin-3 mRNA (left) and 10 protein (right). The results (mean±SD for three replicates) are expressed as the relative galectin-3 mRNA levels (normalized to GAPDH) compared to that obtained with the scrambled miRNA (assigned a value of 1)(left). The asterisk (*) denotes a significant difference at $p<0.OI$ as compared to control (left). 3F—BT549/vector cells were transfected with an antisense 2'-O-methyl oligoribonucleotide targeted against miR-322 or a scrambled 15 2'-O-methyl oligoribonucleotide as a control for 72 h. The cells were analyzed for galectin-3 and GAPDH mRNA levels by quantitative RT-PCR (left) or galectin-3 and ~-actin protein levels by immmunoglotting (right). The RT-PCR results (mean±SD) from three replicates) are expressed as the relative galectin-3 mRNA levels (normalized to GAPDH) compared to that obtained with the scrambled miRNA (assigned a value of 1). The asterisk (*) denotes a 20 significant different at $p<0.OI$ as compared to normal. 3G—BT549IMUCI cells were transfected with a pre-miR-322 or a scrambled miRNA and selected in the presence of blasticidin. Nuclei were assayed for galectin-3 and fJ-actin gene transcription in run-on assays. The results (mean±SD from three replicates) are expressed as the relative change in the abundance of newly transcribed galectin-3 mRNA.

FIGS. 4A, 4B, 4C, 4D, 4E, 4F. Galectin-3 associates with the MUCI-C extracellular domain. 4A—Lysates from ZR-75-1 cells were immunoprecipitated with anti-MUCI-C and, as a control, a non-specific IgG (left). The precipitates were immunoblotted with the indicated antibodies. ZR-75-1 cell lysates were incubated with GST or GST-galectin-3 bound 30 to glutathione beads (right). The adsorbates were immunoblotted with anti-MUCI-C. Input of the GST and GST-galectin-3 proteins was assessed by Coomassie blue staining. 4B Schematic representation of the transmembrane MUCI-C subunit and amino acid sequence of the extracellular domain (MUCI-CIED) (SEQ ID NO:25). 4C—Left. ZR-75-1 cells were grown in 0.1% FBS for 2 days. Cell surface binding proteins were released in salt solution, diluted and passed through hFc or hFc-MUCI-C/EO columns. The adsorbed proteins were eluted and analyzed by SOS-PAGE and silver staining. The 26 kDa protein was subjected to trypsin digestion. Analysis of the tryptic peptides by LC-MS demonstrated identity with galectin-3. Right. hFc 5 and hFc-MUCI-C/EO were incubated with purified galectin-3 and precipitated with protein G-sepharose. The adsorbates were immunoblotted with anti-galectin-3 (upper panel). The input proteins were stained with Coomassie blue (lower panel). 40—Schema of galectin-3 is shown with the regions expressed as GST fusion proteins. hFc-MUCI-CIEO was incubated with GST or the indicated GST-galectin-3 fusion proteins. Adsorbates to glutathione beads 10 were immunoblotted with anti-MUCI-C/EO. Input proteins were stained with Coomassie blue. 4E—hFc-MUC1-CIEO was injected at concentrations ranging from 0 oM to 100 oM at a constant flow rate of 30 Il Vmin over a galectin-3 immobilized chip (4E), over a galectin-3 (63-250) immobilized chip (4F) and over a control dextran surface. The association was monitored for 200 seconds and the dissociation observed for 500 seconds. The dark curve 15 represents the fit of data to 1:1 binding with a drifting base model.

FIGS. 5A, 5B, 5C, 5D, 5E, 5F. Glycosylation of MUC1-C on Asn-36 is necessary for galectin-3 binding. 5A—Lysates from BT549/MUC1 (left) and ZR-75-1 (right) cells were immunoprecipitated with anti-MUC1-C. The precipitates were left untreated or digested with N-glycosidases and then immunoblotted with anti-MUC1-C. 5B—MUC1-C was transiently expressed in wild-type CHO-K1 cells or the glycosylation-deficient Lec1 and Lec8 variants. Lysates were immunoblotted with anti-MUC1-C (left). The lysates were also incubated with GST-galectin-3 and the precipitates immunoblotted with anti-MUC1-C (right). 5C—Lett. Lysates from BT549 cells stably expressing MUC1-C or MUC1-C(N36A) were immunoblotted with anti-MUC1-C. Right. Lysates from BT549/MUC1-C cells were immunoprecipitated with anti-MUC1-C. The precipitates were left untreated or digested with N-glycosidases and immunoblotted with anti-MUC1-C. 5D—Lysates from BT549/MUC1-C and BT549/MUC1-C(N36A) cells were incubated with GST-galectin-3 and the adsorbates were immunoblotted with anti-MUC1-C. 5E—ZR-75-1 cells were incubated with sucrose or lactose in complete medium for 24 h and then with sucrose and lactose for an additional 24 h in 0.1% serum. The cells were then stimulated with EGF for 5 min. 5F—ZR-75-1 cells were transfected with a control siRNA or a galectin-3 siRNA pool for 48 h and then grown in the presence of 0.1% serum for 24 h. The cells were then stimulated with EGF for 5 min. Cells were analyzed by confocal microscopy after fixation and staining with anti-EGFR and anti-MUC1-N.

FIGS. 6A, 6B, 6C, 6D. Glycosylation of MUC1-C on Asn-36 is associated with upregulation of galectin-3 expression. 6A—Lysates from BT549 cells stably expressing the empty vector, MUC1-C or MUC1-C(N36A) were immunoblotted with the indicated antibodies. 6B—The indicated BT549 cells were analyzed for galectin-3 and GAPDH mRNA levels by semi-quantitative RT-PCR (left) and real time RT-PCR (right). The real time RT-PCR results (mean±SD from three replicates) are expressed as the relative galectin-3 mRNA levels (normalized to GAPDH) compared to that obtained with BT549/vector cells (assigned a value of 1). 6C—The indicated BT549 cells were transfected with pMIR-Gal-3(3'UTR) and pMIR-β-gal plasmids. The cells were assayed for luciferase and β-gal activities at 48 h after transfection. The results (mean±SD of three experiments) are expressed as the relative luciferase activity (normalized to β-gal) compared to that in BT549/vector cells. 6D—Northern blot analysis of RNA from the indicated BT549 cells probed for miR-322 and U6 snRNA.

FIGS. 7A, 7B, 7C, 7D. Interaction between MUC1 and EGFR is mediated by galectin-3. 7A—ZR-75-1 cells were incubated with sucrose or lactose in complete medium for 24 h and then with sucrose and lactose for an additional 24 h in 0.1% serum. The cells were then stimulated with EGF for 5 min. 7B—ZR-75-1 cells were transfected with a control siRNA or a galectin-3 siRNA pool for 48 h and then grown in the presence of 0.1% serum for 24 h. The cells were then stimulated with EGF for 5 min. Anti-MUC1-N precipitates were immunoblotted with the indicated antibodies (A and B). Lysates were also directly immunoblotted with anti-galectin-3 (B). 7C, 7D—ZR-75-1 cells were transfected with a pre-miR-322 or a scrambled miRNA and selected in blasticidin. Lysates were immunoblotted with the indicated antibodies (C). Anti-MUC1-N precipitates were immunoblotted with the indicated antibodies (D).

DESCRIPTION OF ILLUSTRATIVE EMBODIMENTS

The MUC1 mucin-type, transmembrane glycoprotein is expressed on the apical borders of normal secretory epithelial cells (Kufe et al., 1984). With transformation and loss of polarity, MUC1 is aberrantly overexpressed on the entire cell surface in carcinomas of the breast, prostate, lung and other epithelia (Kufe et al., 1984). The MUC1 polypeptide undergoes autoproteolysis in the endoplasmic reticulum with the generation of two subunits that in turn form a stable heterodimer (Ligtenberg et al., 1992); Levitin et al., 2005; Macao et al., 2006). The MUC1 N-terminal subunit (MUC1-N) consists in large part of variable numbers of 20 amino acid tandem repeats that are subject to extensive β-glycosylation (Gendler et al., 1988; Siddiqui et al., 1988). MUC1-N is tethered to the cell surface through noncovalent binding to the transmembrane MUC1 C-terminal subunit, which consists of a 58 amino acid extracellular domain, a 28 amino acid transmembrane domain and a 72 amino acid cytoplasmic tail (Merlo et al., 1989). MUC1-N extends beyond the cell glycocalyx as part of a physical barrier that protects epithelial cells from damage induced by free radicals, low pH, toxins and other forms of stress that occur at the interface with the external environment. MUC1-N can also be shed into this protective barrier, leaving MUC1-C at the cell surface as a putative receptor for signaling the presence of stress to the interior of the cell. In this context, overexpression of MUC1 in transformed cells is associated with accumulation of MUC1-C in the cytosol and targeting of this subunit to the nucleus (Li et al., 2003; Li et al., 2003; Li et al., 2003; Wen et al., 2003) and mitochondria (Ren et al., 2004; Ren et al., 2006). In support of a role for MUC1-C in signal transduction, the cytoplasmic domain functions as a substrate for the epidermal growth factor receptor (Li et al., 2001), c-Src (Li et al., 2001) and glycogen synthase 3β (Li et al., 1998). Moreover, the MUC1-C cytoplasmic domain interacts directly with the Wnt pathway effector, β-catenin (Li et al., 1998; Yamamoto et al., 1997; Huang et al., 2005) and with the p53 tumor suppressor (Wei et al., 2005). Studies have demonstrated that overexpression of MUC1 is sufficient to confer resistance to stress-induced apoptosis (Li et al., 2003; Ren et al., 2004; Wei et al., 2005; Raina et al., 2004), anchorage-independent growth and tumorigenicity (Li et al., 2003; Huang et al., 2005; Schroeder et al., 2004). MUC1 associates with EGFR constitutively, and this interaction is stimulated by EGF treatment (Li et al., 2001).

The human MUC1-C polypeptide sequence is:

```
                                            (SEQ ID NO: 1)
SVVVQLTLAFREGTINVHDVETQFNQYKTEAASRYNLTISDVSVSDVPF

PFSAQSGAGVPGWGIALLVLVCVLVALAIVYLIALAVCQCRRKNYGQL

DIFPARDTYHPMSEYPTYHTHGRYVPPSSTDRSPYEKVSAGNGGSSLSY

TNPAVAATSANL
```

Galectins are a family of lectin proteins that contain conserved carbohydrate-recognition domains (CRDs) with specificity for β-galactosides found on both N- and O-linked glycans (Liu and Rabinovich, 2005). Of the fifteen known mammalian galectins, the widely expressed galectin-3 is a structurally unique member with an N-terminal domain of 12 amino acids and repetitive sequences rich in proline, glycine and tyrosine upstream to the CRD. Cytosolic galectin-3 is targeted to the plasma membrane and released into the extracellular space (Hughes (1999) *Biochim. Biophys. Acta.* 1473: 172-185), where it functions in the regulation of cell migration and adhesion (Ochieng (2004) *Glycoconj. J.* 19:527-535). Galectin-3 is also targeted to the nucleus where it plays a role in regulating pre-mRNA splicing (Patterson et al. (2004) *Glycoconj J.* 19:499-506) and contributes to the activation of diverse transcription factors (Lin et al., 2002; Dudas et al., 2002; Walzel et al., 2002; Paron et al., 2003). As with MUC1 (Huang et al., 2003), galectin-3 binds directly to β-catenin and induces the transcriptional activity of Tcf-4 (Shimura et al., 2004). In addition, like MUC1 (Ren et al., 2004; Wei et al., 2005), galectin-3 blocks the apoptotic response of breast cancer cells to genotoxic anti-cancer agents (Takenaka et al., 2004). The anti-apoptotic activity of galectin-3 is regulated by casein kinase 1-mediated phosphorylation of nuclear galectin-3 on Ser-6 (Yoshii et al., 2002) and thereby its export to the cytoplasm (Takenaka et al., 2004). Translocation of galectin-3 to mitochondria with inhibition of cytochrome c release contributes in part to protection against the induction of apoptosis (Matarrese et al., 2000; Yu et al., 2002). Galectin-3 also contains an Asp-Trp-Gly-Arg (NWGR; SEQ ID NO:8) motif that is conserved in the BH1 domain of the Bcl-2 family members and is of importance to the galectin-3 anti-apoptotic function (Akahani et al., 1997). Other studies have demonstrated that galectin-3 induces transformation (Takenaka et al., 2003; Nangia-Makker et al., 1995) and is upregulated in diverse carcinomas (Takenaka et al., 2004). Studies have shown that EGFR is cross-linked at the cell surface by galectin-3 (Partridge et al., 2004).

The human galectin-3 polypeptide sequence is:

(SEQ ID NO: 2)
MADNFSLHDALSGSGNPNPQGWPGAWGNQPAGAGGYPGASYPGAYP

GQAPPGAYPGQAPPGAYHGAPGAYPGAPAPGVYPGPPSGPGAYPSSG

QPSAPGAYPATGPYGAPAGPLIVPYNLPLPGGVVPRMLITILGTVKPNA

NRIALDFQRGNDVAFHFNPRFNENNRRVIVCNTKLDNNWGREERQSV

FPFESGKPFKIQVLVEPDHFKVAVNDAHLLQYNHRVKKLNEISKLGISG

DIDLTSASYTMI

An exemplary carbohydrate-binding domain of galectin-3 includes amino acid residues 117-244 of SEQ ID NO:2.

miRNAs are noncoding RNAs of about 22 nucleotides that post-transcriptionally regulate gene expression. Base-pairing of the miRNA with complementary sequences in a mRNA 3'UTR leads to suppression of translation or decreases in mRNA stability (Bartel (2004). Translational suppression is a more commonly described mechanism of miRNA action; however, there are now an increasing number of reports of miRNA-mediated mRNA degradation (Bagga et al., 2005; Krutzfeldt et al., 2005; Lim et al., 2005; Wu and Belasco, 2005). Binding of the miRNA is associated with accelerated deadenylation of the mRNA (Wu et al., 2006). Herein, miR-322 is identified as a putative regulator of galectin-3 expression that is expressed in human cells. The precursor stem loop sequence for miR-322 is located at chromosome Xq26.3. The genomic annotation specifies overlapping of the miR-322 precursor sequence with the 5'UTR of a hypothetical gene, designated MGC16121, indicating that both the pre-miRNA and the MGC16121 mRNA may originate from the same transcript. In this regard, like miR-322, MUC1 suppresses MGC16121 mRNA levels. Upstream to the MGC16121 5'UTR is a putative promoter with a TATA box and, within 2000 bp, potential binding sites for 39 different transcription factors. The sequence of human miR-322 as deduced from the sequence of the human genome is 5'-AAACGUGAG-GCGCUGCUAUA-3' (SEQ ID NO:4).

Methods of Screening for Inhibitory Compounds

The invention provides in vitro methods for identifying compounds (e.g., small molecules or macromolecules) that inhibit binding of galectin-3 to MUC1-C.

These methods can be performed using: (a) isolated MUC1-C test agents and galectin-3 test agents; (b) cells expressing both a MUC1-C test agent and a galectin-3 test agent; (c) cells expressing a MUC1-C test agent and different cells expressing a galectin-3 test agent; or (d) isolated MUC1-C test agents or galectin-3 test agents and cells expressing a galectin-3 test agent or a MUC1-C test agent.

The term "isolated" as applied to any of the above-listed polypeptide test agents refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a test agent is at least 80%, more preferably at least 90%, and most preferably at least 99%, by dry weight, the test agent. Since a polypeptide that is chemically synthesized is, by its nature, separated from the components that naturally accompany it, a synthetic polypeptide test agent is "isolated."

An isolated polypeptide test agent can be obtained, for example, by extraction from a natural source (e.g., from tissues); by expression of a recombinant nucleic acid encoding the polypeptide; or by chemical synthesis. A polypeptide test agent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the test agents can undergo modification, e.g., phosphorylation or glycosylation, by methods known in the art. The test agents can be modified prior to isolation.

In methods of screening for compounds that inhibit binding of an isolated MUC1-C test agent to an isolated galectin-3 test agent, a MUC1-C test agent is contacted with a galectin-3 test agent in the presence of one or more concentrations of a test compound and binding between the two test agents in the presence and absence of the test compound is detected and/or measured. In such assays neither of the test agents need be detectably labeled. For example, by exploiting the phenomenon of surface plasmon resonance, the MUC1-C test agent can be bound to a suitable solid substrate and the galectin-3 test agent exposed to the substrate-bound MUC1-C test agent in the presence and absence of the compound of interest.

Binding of the galectin-3 test agent to the MUC1-C test agent on the solid substrate results in a change in the intensity of surface plasmon resonance that can be detected qualitatively or quantitatively by an appropriate instrument, e.g., a Biacore™ apparatus (Biacore International AB, Rapsgatan, Sweden). It will be appreciated that the experiment can be performed in reverse, i.e., with the galectin-3 test agent bound to the solid substrate and the MUC1-C test agent added to it in the presence of the test compound.

Moreover, assays to test for inhibition of binding to MUC1-C can involve the use, for example, of: (a) a single MUC1-C-specific "detection" antibody that is detectably labeled; (b) an unlabeled MUC1-C-specific antibody and a detectably labeled secondary antibody; or (c) a biotinylated MUC1-C-specific antibody and detectably labeled avidin. In addition, combinations of these approaches (including "multi-layer" assays) familiar to those in the art can be used to enhance the sensitivity of assays. In these assays, the MUC1-binder test agent can be immobilized on a solid substrate such as a nylon or nitrocellulose membrane by, for example, "spotting" an aliquot of a sample containing the test agent onto a membrane or by blotting onto a membrane an electrophoretic gel on which the sample or an aliquot of the sample has been subjected to electrophoretic separation. Alternatively, the galectin-3 test agent can be bound to a substrate (e.g., the plastic bottom of an ELISA (enzyme-linked immunosorbent assay) plate well) using methods known in the art. The substrate-bound test agent is then exposed to the MUC1-C test agent in the presence and absence of the test compound. After incubating the resulting mixture for a period of time and at temperature optimized for the system of interest, the presence and/or amount of MUC1-C test agent bound to the galectin-3 test agent on the solid substrate is then assayed using a detection antibody that binds to the MUC1-C test agent and, where required, appropriate detectably labeled secondary antibodies or avidin. It will be appreciated that instead of binding the galectin-3 test agent to the solid substrate, the MUC1-C test agent can be bound to it. In this case binding of the galectin-3 test agent to the substrate-bound MUC1-C is tested by obvious adaptations of the method described above for substrate-bound MUC1-binder test agent.

The invention also features "sandwich" assays. In these sandwich assays, instead of immobilizing test agents on solid substrates by the methods described above, an appropriate test agent can be immobilized on the solid substrate by, prior to exposing the solid substrate to the test agent, conjugating a "capture" test agent-specific antibody (polyclonal or mAb) to the solid substrate by any of a variety of methods known in the art. The test agent is then bound to the solid substrate by virtue of its binding to the capture antibody conjugated to the solid substrate. The procedure is carried out in essentially the same manner described above for methods in which the appropriate test agent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays which involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, or $^{14}C$), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, colorimeters, fluorometers, luminometers, and densitometers.

Candidate compounds can also be tested for their ability to inhibit binding of MUC1-C to galectin-3 in cells. The cells can either naturally express an appropriate MUC1-C test agent and/or galectin-3 test agent of interest or they can recombinantly express either or both test agents. The cells can be normal or malignant and of any histological type, e.g., without limitation, epithelial cells, fibroblasts, lymphoid cells, macrophages/monocytes, granulocytes, keratinocytes, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., a growth factor such as EGF) prior to or after exposure of the cells to the compound. Following incubation of cells expressing the test agents of interest in the absence or presence (optionally at various concentrations), physical association between the test agents can be determined microscopically using appropriately labeled antibodies specific for both test agents, e.g., by confocal microscopy. Alternatively, the cells can be lysed under non-dissociating conditions and the lysates tested for the presence of physically associated test agents. Such methods include adaptations of those described using isolated test agents. For example, an antibody specific for one of the two test agents (test agent 1) can be bound to a solid substrate (e.g., the bottom and sides of the well of a microtiter plate or a nylon membrane). After washing away unbound antibody, the solid substrate with bound antibody is contacted with the cell lysate. Any test agent 1 in the lysate, bound or not bound to the second test agent (test agent 2), will bind to the antibody specific for test agent 1 on the solid substrate. After washing away unbound lysate components, the presence of test agent 2 (bound via test agent 1 and the antibody specific for test agent 1 to the solid substrate) is tested for using a detectably labeled antibody (see above) specific for test agent 2. Alternatively, test agent 1 can be immunoprecipitated with an antibody specific for test agent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any test agent 2 on the membrane detected and/or measured with a detectably labeled antibody (see above) specific for test agent 2 by any of the above-described methods. It is understood that in the above-described assays, test agent 1 can be either the MUC1-C test agent or the galectin-3 test agent or vice versa.

Methods of Designing and Producing Inhibitory Compounds

The invention also relates to using MUC1-C test agents and/or galectin-3 test agents to predict or design compounds that can interact with MUC1-C and/or galectin-3 and potentially thereby inhibit the ability of MUC1-C to interact with an appropriate tumor progressor. One of skill in the art would know how to use standard molecular modeling or other techniques to identify small molecules that would bind to "appropriate sites" on MUC1-C and/or tumor progressors. One such example is provided in Broughton (1997). Generally, an "appropriate site" on MUC1-C or galectin-3 is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction in a conformational change in the molecule) in inhibition of the binding of the molecule to another molecule By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to a region of MUC1-C that interacts with galectin-3 (e.g., all or a part of the extracellular domain of MUC1-C) or a region of galectin-3 that binds to MUC1 (e.g., a region within the carbohydrate binding domain and/or all or a part of amino acid residues 63-250) typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., a region of MUC1-C that interacts with galectin-3 or a region of galectin-3 that binds to MUC1-C and/or determine the structures involved in MUC1-C/galectin-3 binding. Computer programs such as INSIGHT™ (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing an inhibitory compound can involve:

(a) inputting into an input device, e.g., through a keyboard, a diskette, or a tape, data (e.g. atomic coordinates) that define the three-dimensional (3-D) structure of a first molecule (e.g., MUC1-C or a part of MUC1-C) that binds to a second molecule (e.g., galectin-3 or a part thereof) or a molecular complex (e.g., MUC1-C, or a part thereof, bound to galectin-3, or a part thereof), e.g., a region of MUC1-C that interacts with galectin-3 (e.g., all or a part of the extracellular domain of MUC1-C), the region of galectin-3 that binds to MUC1-C (e.g., a region within the carbohydrate binding domain and/or all or part of amino acid residues 63-250), or all or a part (e.g., the cytoplasmic domain) of MUC1-C bound to all or a part (e.g., the carbohydrate binding domain and/or amino acid residues 63-250) of galectin-3; and (b) determining, using a processor, the 3-D structure (e.g., an atomic model) of: (i) the site on the first molecule involved in binding to the second molecule; or (ii) one or more sites of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic data) for a candidate compound are available, the following computer-based steps can be performed in conjunction with computer-based steps (a) and (b) described above:

(c) inputting into an input device, e.g., through a keyboard, a diskette, or a tape, data (e.g. atomic coordinates) that define the three-dimensional (3-D) structure of a candidate compound;

(d) determining, using a processor, the 3-D structure (e.g., an atomic model) of the candidate compound;

(e) determining, using the processor, whether the candidate compound binds to the site on the first molecule or the one or more sites on the molecular components of the molecular complex; and (f) identifying the candidate compound as compound that inhibits the interaction between the first and second molecule or the between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1-C, the extracellular domain of MUC1-C, galectin-3, or the carbohydrate binding domain of galectin-3) stored in a data storage system.

Compounds of the invention also may be interactively designed from structural information of the compounds described herein using other structure-based design/modeling techniques (see, e.g., Jackson, 1997; and Jones et al., 1996). Compounds and polypeptides of the invention also can be identified by, for example, identifying candidate compounds by computer modeling as fitting spatially and preferentially (i.e., with high affinity) into the appropriate acceptor sites on MUC1-C or galectin-3.

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000-fold, or 100,000-fold) more of a given MUC1-C test agent to achieve a defined arbitrary level of binding to a fixed amount of a galectin-3 test agent than is achieved in the absence of the compound can be useful for inhibiting the interaction between MUC1-C and galectin-3, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000-fold, or 100,000-fold) more of a given galectin-3 test agent to achieve a defined arbitrary level of binding to a fixed amount of a MUC1-C test agent than is achieved in the absence of the compound can be useful for inhibiting the interaction between MUC1-C and galectin-3, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al., 1990; Navia et al., 1992, the disclosures of which are incorporated herein by reference in its entirety]. All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

Structure determination by x-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up the work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds it's solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M Hepes, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. application Ser. No. 10/486,278, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: *Protein NMR Spectroscopy, Principles and Practice*, 1996; Gronenborn et al., 1990; and Wider (2000), supra., the disclosures of all of which are incorporated herein by reference in their entirety Any available method can be used to construct a 3-D model of a region of MUC1-C and/or galectin-3 from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., from Silicon Graphics, Evans and Sutherland, SUN, Hewlett Packard, Apple Macintosh, DEC, IBM, or Compaq.

Methods of Making Inhibitory Compounds and Proteins Useful for the Invention

Once the 3-D structure of a protein of interest (MUC1-C or galectin-3), or a binding region-containing fragment thereof, has been established using any of the above methods, a compound that has substantially the same 3-D structure (or contains a domain that has substantially the same structure) as the binding region of the protein of interest. The compound's structure can be based on the 3-D structure of binding site of the parent protein (e.g., MUC1-C), the 3-D structure of the complementary acceptor site of the protein to which the parent protein binds (e.g., galectin-3), or a combination of both. In this context, "has substantially the same 3-D structure" means that the compound binds with at least the same avidity as the parent protein to the non-parent partner. The compound can also bind to the non-parent partner with at least two-fold (at least: three-fold; four-fold; five-fold; six-fold; seven-fold; eight-fold; nine-fold; ten-fold; 20-fold; 50-fold; 100-fold; 1,000-fold; 10,000-fold; 100,000-fold; 1,000,000-fold; or even higher-fold) greater avidity than the parent protein. One of skill in the art would know how to test a compound for such an ability.

With the above described 3-D structural data on hand and knowing the chemical structure (e.g., amino acid sequence in the case of a protein) of the protein region of interest, those of skill in the art would know how to make compounds with the above-described properties. Such methods include chemical synthetic methods and, in the case of proteins, recombinant methods (see above). For example, cysteine residues appropriately placed in a compound so as to form disulfide bonds can be used to constrain the compound or a domain of the compound in an appropriate 3-D structure. In addition, in a compound that is a polypeptide or includes a domain that is a polypeptide, one of skill in the art would know what amino acids to include and in what sequence to include them in order to generate, for example, α-helices, β structures, or sharp turns or bends in the polypeptide backbone.

Of particular interest as small molecule compounds are nucleic acid aptamers which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) [see, for example, Zhang et al. (2004), the disclosure of which is incorporated herein by reference in its entirety]. For methods of enhancing the stability (by using nucleotide analogs, for example) and enhancing in vivo bioavailability (e.g., in vivo persistence in a subject's circulatory system) of nucleic acid aptamers see Zhang et al. (2004) supra and Brody et al. (2000), the disclosure of which is incorporated herein by reference in its entirety].

While not essential, computer-based methods can be used to design the compounds of the invention. Appropriate computer programs include: LUDI (Biosym Technologies, Inc., San Diego, Calif.), Aladdin (Daylight Chemical Information Systems, Irvine, Calif.); and LEGEND (Nishibata et al., 1985).

The compounds of the invention can include, in addition, to the above described proteins, one or more domains that facilitate purification (e.g., poly-histidine sequences) or domains that serve to direct the compound to appropriate target cells (e.g., cancer cells), e.g., ligands or antibodies (including antibody fragments such as Fab, F(ab')$_2$, or single chain Fv fragments) specific for cell surface components of target cells of the immune system, e.g., MUC1-C, galectin-3, Her2/Neu, or any of a variety of other tumor-associated antigens. Signal sequences that facilitate transport of the compounds across biological membranes (e.g., cell membranes and/or nuclear membranes) and/direct them to subcellular compartments can also be linked (e.g., covalently) to the compounds. Exemplary signal sequences are described in detail in U.S. Pat. No. 5,827,516, the disclosure of which is incorporated herein by reference in its entirety. All that is required in such multidomain compounds is that the domain corresponding to the parent inhibitory compound substantially retains the 3-D structure it would have in the absence of the additional domains. Conjugation to make such multidomain compounds can be by chemical methods [e.g., Barrios et al. (1992), the disclosure of which is incorporated herein by reference in its entirety]. Where the compound is a peptide, it can be produced as part of a recombinant protein, such as one that self-assembles into virus-sized particles (e.g., U.S. Pat. No. 4,918,166, the disclosure of which is incorporated herein by reference in its entirety) that display candidate binding peptides on the surface.

Compounds of the invention that are peptides also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of compounds of the invention that are peptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to inhibit the interaction between MUC1-C and galectin-3. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

The proteins (MUC1-C or galectin-3) used for designing compounds of the invention and all other methods described herein can be purified from natural sources (e.g., from tissues such as pancreas, liver, lung, breast, skin, spleen, ovary, testis, muscle, joint tissue, neural tissue, gastrointestinal tissue or tumor tissue (e.g., breast cancer or colon cancer tissue), or body fluids such as blood, serum, or urine). Smaller peptides (fewer than 100 amino acids long) and other non-protein compounds of the invention can be conveniently synthesized by standard chemical means known to those in the art. In addition, both polypeptides and peptides can be manufactured by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al. (1989), and Ausubel et al. (1989).

For the structural (e.g., x-ray crystallographic and NMR) analyses described above, it is generally required that proteins, or fragments thereof, be highly purified. Methods for purifying biological macromolecules (e.g., proteins) are known in the art. The degree of purity of proteins can be measured by any appropriate method, e.g., column chromatography, polyacrylamide gel electrophoresis, or HPLC analysis.

MUC1-C and galectin-3 used for the above analyses can be of any mammalian species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

Methods of Inhibiting Binding of MUC1-C to Galectin-3 in or on a Cell

The invention features methods of inhibiting binding of MUC1-C to galectin-3 in or on a cell. The method involves introducing to the surface of, or into, the cell a compound that inhibits the binding of galectin-3 to MUC1-C (e.g., to the MUC1 ED). Prior to introduction of the compound to or into the cell, the cell (or another cancer cell from the subject from which the cell to be treated was obtained) can optionally be tested for MUC1 expression. This can be done by testing for expression of either MUC1 protein or MUC1 mRNA by any of a wide variety of methods known in the art.

The compound can be one identified by the methods described above. Examples of appropriate compounds include the ED of human MUC1-C, peptide fragments of the ED of MUC1-C that bind to galectin-3, and fragments of galectin-3 that bind MUC1-C. An appropriate fragment of the human MUC1-C can be one containing or consisting of all or part of amino acids 1-58 of SEQ ID NO:1. Other useful inhibitory compounds can be molecules that contain or consist of all or part of amino acids 63-250 or 117-244 of galectin-3 (SEQ ID NO:2).

Peptide inhibitory compounds can contain up to 50 (e.g., one, two, three, four, five, six, seven, eight, nine, ten, 12, 15, 18, 20, 25, 30, 35, 40, 45, or 50) MUC1 or galectin-3 residues or unrelated residues on either end or on both ends of the MUC1 or galectin-3 inhibitory segments.

Any MUC1 or galectin-3 peptides to be used as inhibitor compounds can optionally have any phosphorylation-susceptible amino acid residues phosphorylated, e.g., S6 of SEQ ID NO:2. Any MUC1-C peptides to be used as inhibitor compounds can optionally be glycosylated on a residue corresponding to N36 of SEQ ID NO:1.

MUC1 peptide fragments useful as inhibitory compounds (or other inhibitory compounds (e.g., galectin-3-specific antibodies or antibody fragments) that act by binding galectin-3) will have substantially no MUC1 agonist activity, i.e., they will substantially lack the effects of MUC1 described herein that result from binding of MUC1-C to galectin-3. Compounds having substantially no MUC1 agonist activity are those having less than 20% (e.g., less than: 10%; 5%; 2%; 1%; 0.5%; 0.2%; 0.1%; 0.01%; 0.001%; or 0.0001%) of the ability of MUC1-C to increase the mRNA level of galectin-3.

Similarly, galectin-3 peptide fragment compounds will have substantially none of the expression-enhancing activity of galectin-3 on the galectin-3 gene that occurs in the presence of nonlimiting amounts of MUC1. Compounds having substantially none of the activity of galectin-3 that occurs in the presence of nonlimiting amounts of MUC1, have less than 20% (e.g., less than: 10%; 5%; 2%; 1%; 0.5%; 0.2%; 0.1%; 0.01%; 0.001%; or 0.0001%) of galectin-3 to increase the mRNA level of galectin-3. Methods of designing, making, and testing such compounds for the appropriate binding-inhibitory activity are known to those in the art.

In addition, the inhibitory compounds can be antibodies, or antigen-binding antibody fragments, specific for MUC1 or galectin-3. Such antibodies will generally bind to, or near to: (a) the region of MUC1 to which galectin-3 binds; (b) or the region on galectin-3 to which MUC1 binds. However, as indicated above, the compounds can also act allosterically and so they can also bind to the three proteins at positions other than, and even remote from, the binding sites for MUC1 (on galectin-3) and on galectin-3 (for MUC1). As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies (Poljak, 1994; Hudson et al., 1999, the disclosures of both of which are incorporated herein by reference in their entirety) and intrabodies (Huston et al., 2001; Wheeler et al., 2003; Stocks, 2004, the disclosures of all of which are incorporated herein by reference in their entirety] can be used in the methods of the invention).

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1991) the disclosure of which is incorporated herein by reference in their entirety. scFv fragments can be produced, for example, as described in U.S. Pat. No. 4,642,334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al., 1988; Liu et al., 1987; Sun et al., 1987; Nishimura et al., 1987; Wood et al., 1985; Shaw et al., 1988; Morrison, 1985; Oi et al., 1986; Winter, U.S. Pat. No. 5,225,539; Jones et al., 1986; Veroeyan et al., 1988; and Beidler et al., 1988). The disclosures of all these articles and patent documents are incorporated herein by reference in their entirety.

Other compounds useful to inhibit the binding of MUC1-C to galectin-3 include β-galactoside carbohydrates (e.g., lactose) and carbohydrate analogs that bind to galectin-3 (see, e.g., Ahmad et al., 2004).

Also useful for inhibiting the binding of MUC1-C to galectin-3 are compounds capable of deglycosylating MUC1 (e.g., deglycosylating enzymes) or capable of inhibiting the glycosylation (e.g., N-glycosylation) of MUC1 (e.g., tunicamycin).

Compounds that inhibit the binding of galectin-3 to the extracellular domain of MUC1-C can also be useful for inhibiting the association of MUC1 and EGFR in cells (e.g., cancer cells) that express MUC1.

Cells to which the method of the invention can be applied include generally any cell that expresses MUC1. Such cells include normal cells, such as any normal epithelial cell, or a cancer cell, whose proliferation it is desired to inhibit. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. It will be appreciated that proteins (e.g., galectin-3 and MUC-1), fragments thereof, and other compounds recited herein as useful for the invention can be of any of these species.

The methods can be performed in vitro, in vivo, or ex vivo. In vitro application of appropriate compounds can be useful, for example, in basic scientific studies of tumor cell biology, e.g., studies on the mechanism of action of MUC1 and/or galectin-3 in promoting tumor cell growth, including survival. In addition, the compounds that are inhibitory can be used as "positive controls" in methods to identify additional compounds with inhibitory activity (see above). In such in vitro methods, cells expressing MUC1 and galectin-3 can be incubated for various times with the inhibitory compound(s) at a variety of concentrations. Other incubation conditions known to those in art (e.g., temperature, or cell concentration) can also be varied Inhibition of binding can be tested by methods such as those disclosed herein.

The methods of the invention will preferably be in vivo or ex vivo.

Compounds that inhibit binding between MUC1 and galectin-3 are generally useful as cancer cell (e.g., breast cancer cell) survival-inhibiting and/or cell cycle-arresting therapeutics or prophylactics. They can be administered to mammalian subjects (e.g., human breast cancer patients) alone or in conjunction with other drugs and/or radiotherapy. The compounds can also be administered to subjects that are genetically and/or due to, e.g., physiological and/or environmental factors, susceptible to cancer (e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke)). As used herein, a compound that is "therapeutic" is a compound that causes a complete abolishment of the symptoms of a disease or a decrease in the severity of the symptoms of the disease. "Prevention" means that symptoms of the disease (e.g., cancer) are essentially absent. As used herein, "prophylaxis" means complete prevention of the symptoms of a disease, a delay in onset of the symptoms of a disease, or a lessening in the severity of subsequently developed disease symptoms.

When the methods are applied to subjects with cancer, prior to administration of a compound, the cancer can optionally be tested for MUC1 expression and/or galectin-3 expression (e.g., protein or mRNA expression) by methods known in the art. In this way, subjects can be identified as having a MUC1- or galectin-3-expressing cancer. Such methods can be performed in vitro on cancer cells obtained from a subject (e.g., by biopsy). Alternatively, in vivo imaging techniques using, for example, radiolabeled antibodies specific for MUC1 or galectin-3 can be performed. In addition, body fluids (e.g., blood or urine) from subjects with cancer can be tested for elevated levels of MUC1 or galectin-3 protein or protein fragments.

A cell from a subject (e.g., a suspected cancer cell) can be tested for galectin-3 expression (e.g., protein or mRNA expression) and/or expression of a MUC1-galectin-3 protein complex by methods known in the art. An elevated level of galectin-3 or a MUC1-galectin-3 complex (e.g., compared to a reference standard or another cell of the subject) is an indication that the cell is a cancer cell. These methods can be used in diagnosis of cancers.

Cell-Based Methods

In some instances, cells can be tested for MUC1 expression and/or galectin-3 expression (e.g., protein or mRNA expression) by methods known in the art. Such methods can be performed in vitro on cancer cells obtained from a subject (e.g., by biopsy). Alternatively, in vivo imaging techniques using, for example, radiolabeled antibodies specific for MUC1 or galectin-3 can be performed.

Cells (e.g., in vitro or in vivo) that express MUC1 can be more susceptible to apoptosis when galectin-3 is dephosphorylated. Apoptosis can be promoted in such a cell by contacting the cell with a compound that inhibits phosphorylation of galectin-3 (e.g., on Ser6) by casein kinase 1. Exemplary compounds are described (Chijiwa et al., 1989; Meggio et al., 1990; Mashhoon et al., 2000; and Rena et al., 2004).

In Vivo Approaches

In one in vivo approach, a compound that inhibits binding of MUC1 to galectin-3 is administered to a subject. Generally, the compounds of the invention will be suspended in a pharmaceutically-acceptable carrier (e.g., physiological saline) and administered orally or injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al., (1995, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells [see U.S. Pat. Nos. 5,565,334 and 5,874,415, the disclosures of which are incorporated herein by reference in their entirety]. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Ex Vivo Approaches

An ex vivo strategy can involve transfecting or transducing cells, optionally but not necessarily obtained from the subject to be treated, with a polynucleotide encoding a polypeptide that inhibit binding of MUC1 to galectin-3. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells, preferably obtained from the subject but potentially from an individual other than the subject, can be transfected or transformed by a vector encoding the inhibitory polypeptide. The tumor cells, preferably treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits inhibit binding of MUC1 to galectin-3 or glycosylation of MUC1. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the subject or another subject.

Methods of Inhibiting Expression of MUC1 or Galectin-3 in a Cell

Also included in the invention are methods of inhibiting expression of MUC1 or galectin-3 in cells. The method involves introducing into a cell an inhibiting oligonucleotide such as: (a) an antisense oligonucleotide that hybridizes to a MUC1 or galectin-3 transcript, the antisense oligonucleotide inhibiting expression of MUC1 or galectin-3 in the cell, (b) a MUC1 or galectin-3 small interference RNA (siRNA), or (c) a MUC1 or galectin-3 microRNA (miRNA).

The cells and species to which these methods are applied are the same as those recited above in "Methods of Inhibiting Binding of MUC1 to Galectin-3 in or on a Cell."

Prior to introduction of an inhibiting oligonucleotide into the cell, the cell (or another cancer cell from the subject from which the cell to be treated was obtained) can optionally be tested for expression of MUC1 or galectin-3 as described above.

Antisense oligonucleotides hybridize to MUC1 or galectin-3 transcripts and have the effect in the cell of inhibiting expression of the protein translated from the relevant transcripts or of a protein whose expression is regulated by the first protein. Thus, for example, expression of galectin-3 can be inhibited by inhibition of expression of MUC1 Inhibiting expression of MUC1 or galectin-3 in a cell can inhibit cancer cell survival as well as other cancer-enhancing activities associated with MUC1 or galectin-3 expression, e.g., cancer cell proliferation and defective adhesion of cancer cells to neighboring cells. The method can thus be applied to the therapy of cancer, including metastasis.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with a antisense compound is chosen. Thus, for example, for modulation of polyadenylation a preferred target site on an mRNA target is a polyadenylation signal or a polyadenylation site. For diminishing mRNA stability or degradation, destabilizing sequences are preferred target sites. Once one or more target sites have been identified, oligonucleotides are chosen which are sufficiently complementary to the target site (i.e., hybridize sufficiently well under physiological conditions and with sufficient specificity) to give the desired effect.

The miR-322 miRNA has been identified herein as an inhibitor of galectin-3 mRNA stability. The human miR-322 miRNA nucleotide sequence is AAACGUGAGGCGCUGC-UAUA (SEQ ID NO:4). Mouse and rat miR-322 miRNAs have also been identified (see FIG. 3B). Expression of miR-322 miRNA is inhibited by MUC1-C (e.g., N-glycosylated MUC1-C).

With respect to this invention, the term "oligonucleotide" refers to an oligomer or polymer of RNA, DNA, a combination of the two, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

The methods of the invention can be in vitro or in vivo. In vitro applications of the methods can be useful, for example, in basic scientific studies on cancer cell growth, survival, and metastasis. Moreover, since studies described herein show that inhibiting MUC1 or galectin-3 expression resulted in enhanced activity of genotoxic chemotherapeutic agents, they can be used in screening, for example, genotoxic compounds for cancer chemotherapeutic efficacy. In such in vitro methods, appropriate cells (e.g., those expressing MUC1 or galectin-3), can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied Inhibition of MUC1 or galectin-3 expression or cancer cell survival can be tested by methods known to those in the art, e.g., methods such as those disclosed herein. However, the methods of the invention will preferably be in vivo.

The antisense methods are generally useful for cancer cell (e.g., breast cancer cell) survival-inhibiting, proliferation-inhibiting, and/or metastasis-inhibiting therapy. They can be administered to mammalian subjects (e.g., human breast cancer patients) alone or in conjunction with other drugs and/or radiotherapy. Prior to administration of an antisense oligonucleotide to a subject with cancer, the subject can be identified as having a cancer in which the cancer cells express MUC1. Methods for testing this are described above. Doses, formulations, routes of administration, vectors, and targeting are as described for in vivo approaches to inhibiting the binding of MUC1 to MUC-1-binders in a cell. Naturally, the antisense oligonucleotides and expression vectors containing nucleic acid sequences encoding the antisense oligonucleotides will preferably be targeted to cells whose survival and/or growth arrest it is desired to inhibit.

The invention also includes both in vivo and in vitro methods of inhibiting expression of MUC1 that involve the use of compounds (small interference (si)RNA, miRNA, or other small molecules) that inhibit transcription of the MUC1 or galectin-3 gene, stability of the MUC1 or galectin-3 mRNA, and/or translation of MUC1 or galectin-3 mRNA by non-antisense mechanisms. In vitro methods are essentially the same as those described above for antisense methods. In vivo methods involve administration to any of the subjects and by any of the doses and routes disclosed herein. Subjects will preferably be those with cancer, e.g., human cancer patients. Doses, formulations, routes of administration, vectors, and targeting are as described for in vivo antisense approaches. While the invention is not limited by any particular mechanism of action, such compounds can be those that act by either inhibiting the binding and/or the activity of transcription factors or by altering the stability of MUC1 or galectin-3 mRNA.

Double-stranded small interference RNA (siRNA) homologous to MUC1 or galectin-3 DNA can be used to reduce expression of MUC1 or galectin-3 in cancer cells. See, e.g., Fire et al. (1998); Romano and Masino (1992); Cogoni et al. (1996); Cogoni and Masino (1999); Misquitta and Paterson (1999); and Kennerdell and Carthew (1998). The disclosures of all these articles are incorporated herein by reference in their entirety.

The sense and anti-sense RNA strands of siRNA can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. Some of the nucleotides (e.g., the terminal (either terminus) one, two, three, or four nucleotides) can also be deoxyribonucleotides. The sense or anti-sense strand can also be produced biologically using an expression vector into which a target MUC1 or galectin-3 sequence (full-length or a fragment) has been subcloned in a sense or anti-sense orientation. The sense and anti-sense RNA strands can be annealed in vitro before delivery of the dsRNA to cells. Alternatively, annealing can occur in vivo after the sense and anti-sense strands are sequentially delivered to tumor cells and/or tumor-infiltrating leukocytes.

Of interest are siRNA that target, for example, the MUC1 gene sequence 5'-AAGTTCAGTGCCCAGCTCTAC-3' (SEQ ID NO:9). The sense strand of such a siRNA could have the sequence 5'-GUUCAGUGCCCAGCUCUACUU-3' (SEQ ID NO:10) or 5'-GUUCAGUGCCCAGCUC-UACdTdT-3' (SEQ ID NO:11) and the antisense strand could have the sequence 5'-GUAGAGCUGGGCACUGAACUU-3' (SEQ ID NO:12) or 5'-GUA-GAGCUGGGCACUGAACdTdT-3' (SEQ ID NO:13). Also useful is a siRNA containing the MUC1 sequence 5'-GGUACCAUCAAUGUCCACG-3' (sense strand; SEQ ID NO:14) and 5'-CGUGGACAUUGAUGGUACC-3' (antisense strand; SEQ ID NO:15).

Double-stranded siRNA interference can also be achieved by introducing into cells (e.g. cancer cells) a polynucleotide from which sense and anti-sense RNAs can be transcribed under the direction of separate promoters, or a single RNA molecule containing both sense and anti-sense sequences can be transcribed under the direction of a single promoter.

In any of the above methods of inhibiting the interaction between MUC1 and galectin-3 and of inhibiting expression of MUC1 and/or galectin-3, one or more agents (e.g., two, three, four, five, six, seven, eight, nine, ten, 11, 12, 15, 18, 20, 25, 30, 40, 50, 60, 70, 80, 100, or more) including, for example, inhibitory compounds, antisense oligonucleotides, siRNA, miRNA, drugs, aptamers, or other small molecules (or vectors encoding them), can be used.

The above methods of inhibiting MUC1 expression can further be used to inhibit expression of galectin-3 in a cell, e.g., a cancer cell (e.g., a breast cancer cell). See Examples 2 and 3.

The above in vivo and ex vivo methods of inhibiting interactions between MUC1 and galectin-3 and inhibiting expression of MUC1 and/or galectin-3 can be used in conjunction with any of a variety of other cancer therapeutic/prophylactic regimens (e.g., chemotherapeutic, radiotherapeutic, biotherapeutic/prophylactic, and immunotherapeutic/prophylactic regimens). Of particular interest are regimens involving genotoxic (DNA-damaging) agents. Such agents include various forms of ionizing and non-ionizing radiation and a variety of chemotherapeutic compounds.

Non-ionizing radiation includes, for example, ultra-violet (UV) radiation, infra-red (IR) radiation, microwaves, and electronic emissions. The radiation employed in the methods of the invention is preferably ionizing radiation. As used herein, "ionizing radiation" means radiation composed of particles or photons that have sufficient energy or can produce sufficient energy by atomic nuclear interactions to produce ionization (gain or loss of electrons) of an atom. Ionizing radiation thus includes, without limitation, $\alpha$-radiation, $\beta$-radiation, $\gamma$-radiation, or x-radiation. A preferred radiation is x-radiation.

Ionizing radiation causes DNA damage and cell killing generally in proportion to the dose administered. It has been indicated that the multiple biological effects induced by ionizing radiation are due either to the direct interaction of the radiation with DNA or to the formation of free radical species which lead to damage of DNA. These effects include gene mutations, malignant transformation, and cell killing.

External and internal means for delivering ionizing radiation to a target tissue or cell are known in the art. External sources include $\beta$ or $\gamma$ sources or linear accelerators and the like. Alternatively, ionizing radiation may be delivered, for example, by administering a radiolabeled antibody that is capable of binding to a molecule expressed on the surface of a carcinoma (e.g., MUC1 or Her2/neu) to a subject, or by implantation of radiation-emitting pellets in or near the tumor (brachytherapy).

The amount of radiation (e.g., ionizing radiation) needed to kill a given cell generally depends upon the nature of the cell. As used herein, an "effective dose" of radiation means a dose of radiation that produces cell damage or death when given in conjunction with an adenoviral vector of the invention. Means of determining an effective dose are known in the art. X-radiation dosages range from daily doses of 50 to 200 roentgens for prolonged periods of time (e.g., 6-8 weeks or even longer) to single doses of 2,000 to 6,000 roentgens. Dosages for administered radioisotopes vary widely, and depend on the half-life of the isotope, the strength and type of radiation emitted, and the degree of uptake by the target cells.

As used herein, "chemotherapeutic agents" are chemical compounds that enter cells and damage DNA. Thus, they can be compounds which, for example, directly cross-link DNA (e.g., cisplatin (CDDP) and other alkylating agents), intercalate into DNA, or interfere with DNA replication, mitosis, or chromosomal segregation, e.g., adriamycin (also known as doxorubicin), VP-16 (also known as etoposide), verapamil, podophyllotoxin, and the like. These compounds are widely used in the treatment of carcinomas. Chemotherapeutic agents useful in the methods of the invention include, without limitation, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verapamil, podophyllotoxin, tamoxifen, taxol, transplatinum, 5-fluorouracil, vincristin, vinblastin, methotrexate, or any analog or derivative of these that is effective in damaging DNA.

Routes of administration are the same as those disclosed herein for interaction-inhibiting and expression-inhibiting compounds. Doses and frequency of administration vary widely according to all the variables listed above for administration of interaction-inhibiting and expression-inhibiting compounds. For example, adriamycin can be administered by bolus intravenous injection at doses in the range of 25-75 mg/m$^2$ and etoposide can be administered intravenously or orally at doses in the range of 35-100 mg/m². Methods of determining optimal parameters of administration are well known in the art.

Combination treatments can include administration of one or more (e.g., one, two, three, four, five, six, seven, eight, nine or ten) interaction-inhibiting and/or expression-inhibiting compounds of the invention, and one or more (e.g., one, two, three, four, five, six, seven, eight, nine or ten) radiation modalities, and/or one or more (e.g., one, two, three, four, five, six, seven, eight, nine or ten) chemotherapeutic agents. The interaction-inhibiting and expression-inhibiting compounds, radiation treatments and chemotherapeutic agents can be given in any order and frequency. They can be given simultaneously or sequentially. Treatment with any one of the modalities (interaction-inhibiting and expression-inhibiting compounds, radiation, or chemotherapeutic agents) can involve single or multiple (e.g., two, three, four, five, six, eight, nine, ten, 12, 15, 20, 30, 40, 50, 60, 80, 100, 200, 300, 500, or more) administrations separated by any time period found to be optimal in terms of therapeutic benefit. Multiple administrations can be separated by one to 23 hours, a day, two, three days, four days, five days, six days, seven days, eight, ten days, twelve days, two weeks, three weeks four weeks, a month, two months, three months, four months, five months, six months, seven months, eight months, nine months, ten months, eleven months, a year, one and one half of a year, two years, three years, five years, or ten years. Administrations can be continued for as long as the subject is need of the treatment, e.g., any of the of the above time intervals, and can be for the life of the subject. Administrations can be, for example, once a week for the life-time of the subject. When administrations of any or all of the modalities are multiple, the course of any one can be simultaneous with, overlapping with, or consequent to the course(s) of the other(s).

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. Human breast cancer (ZR-75-1, BT549) and lung cancer (CRL-5985, CRL-5909) cells were grown in RPMI1640 medium supplemented with 10% fetal bovine serum (FBS), 100 units/ml penicillin and 100 μg/ml streptomycin. The human breast cancer (MD-MB-431, MCF-7), prostate cancer (LnCAP, DU145, PC3), lung cancer (A549), kidney epithelial (293) and Chinese hamster ovary (CHO-K1) cells were cultured in Dulbecco's Modified Eagle's medium (DMEM) supplemented with 10% FBS, antibiotics and 1 mM L-glutamine. The glycosylation deficient CHO-Lec2 and CHO-Lec8 cells (ATCC, Manassas, Va.) were grown in alpha minimum essential medium containing 10% FBS and antibiotics. In certain studies, cells were cultured in medium with 0.1% FBS for 24 hours and then stimulated with 100 ng/ml epidermal growth factor (EGF) (Calbiochem-Novabiochem, La Jolla, Calif.) for 5 minutes at 37° C.

Immunoblotting and precipitates. Lysates were prepared from subconfluent cells as described (Li et al., 2001). Immunoblot analysis was performed with antibodies specific for MUC1-C (Ab5; Neomarkers, Fremont, Calif.), galectin-3 (Abcam, Cambridge, Mass.), β-actin (Sigma-Aldrich, St. Louis, Mo.), epidermal growth factor receptor (EGFR) (Santa Cruz Biotechnology, Santa Cruz, Calif.), and MUC1-N (DF3) (Ren et al., 2004). Immune complexes were prepared as described with antibodies specific for MUC1-C and MUC1-N (Li et al., 1998). For GST "pull-down" assays, GST or GST-galectin-3 was incubated with cell lysates for 2 hours at 4° C. and precipitated with glutathione-Sepharose™ 4B. Precipitates were subjected to immunoblotting with anti-MUC1-C, anti-galectin-3 (Santa Cruz Biotechnology, Santa Cruz, Calif.), anti-MUC1-N (DF3) (Ren et al., 2004), anti-EGFR (Santa Cruz Biotechnology), or anti-β-actin.

Plasmid constructions. The pIRESpuro2-MUC1 and pIRESpuro2-MUC1-C vectors have been described (Huang et al. (2003); Li et al. (2001)). pRNA-U6.1/Neo-MUC1siRNA plasmids were constructed by ligation of MUC1siRNA#2 (AAGGTACCATCAATGTCCACG (SEQ ID NO:3), MUC1siRNA#4 (AAGTTCAGTGCCAGCTC-TAC (SEQ ID NO:5) or random control (CsiRNA; CGCT-TACCGATTCAGAATGG (SEQ ID NO:6) sequences into pRNA-U6.1 (GenScript). pCR3.1-hFc-MUC1-C extracellular domain (MUC1-C/ED) was constructed by PCR amplification of MUC1-C/ED from pIRESpuro2-MUC1-C and cloned into the mammalian pCR3.1 vector. The human Fc fragment (hFc) was amplified from the CD5-IgG1 plasmid (Aruffo et al., 1990). The N36A mutation in pIRESpuro2-MUC1-C was introduced using the QuickChange™ kit (Stratagene, La Jolla, Calif.). For vectors encoding galectin-3 and galectin-3 fragments, cDNAs were synthesized from ZR-75-1 mRNA using specific primers and cloned into the PET22b+ vector (Novagen, San Diego, Calif.). The plasmids expressing GST-galectin-3 or GST-galectin-3 fragments were generated by PCR from PET22b+-galectin-3 and cloned into the pGEX4T1 vector (Amersham Pharmacia Biotech, Piscataway, N.J.). The galectin-3 promoter regions spanning −3000 to +141 and −836 to +141 by from the transcription start site were amplified using the failsafe PCR kit (Epicentre, Madison, Wis.) and cloned into the pGL3 basic vector NheI and HindIII sites. The galectin-3 3'-UTR was cloned into the pMIR reporter plasmid (Ambion, Austin, Tex.).

In vitro binding assays. hFc and hFc-MUC1-C/ED were incubated with purified galectin-3 in lysis buffer for 1 hour at 4° C. The reaction products were precipitated with protein G-Sepharose™ and immunoblotted with anti-galectin-3. In other studies, hFc-MUC1-C/ED was incubated with GST-galectin-3 deletion mutants. The reaction products were precipitated with glutathione-sepharose 4B and immunoblotted with anti-MUC1-C/ED (Ren et al., 2004).

Cell transfections. pIRESpuro2, pIRESpuro2-MUC1, pIRESpuro2-MUC1-C and pIRESpuro2-MUC1-C(N36A) were transfected into BT549 cells with FuGENE™ 6 reagent (Roche, Basel, Switzerland) and stable clones were selected in the presence of 300 ng/ml puromycin (Calbiochem-Novabiochem, La Jolla, Calif.). The pCR3.1-hFc-MUC1-C/ED plasmid was transfected into CHO-K1 cells with FuGENE™ 6 reagent and selected in the presence of 1 mg/ml G418 (Invitrogen, Carlsbad, Calif.). ZR-75-1 cells were stably transfected to express an empty vector of a MUC1 siRNA as described (Ren et al., 2004). Transient transfections with a MUC1 siRNA pool, galectin-3 siRNA pool, or a non-specific control duplex IX RNA (Dharmacon, Lafayette, Colo.) were performed in the presence of Lipofectamine™ 2000 (Invitrogen, Carlsbad, Calif.). DU145 cells were transfected with pRNA-U6.1/Neo-CsiRNA, pRNA-U6.1/Neo-MUC1siRNA#2 or pRNA-U6.1/Neo-MUC1 siRNA#4 and selected in 200 µg/ml neomycin. DU145/MUC1 siRNA#4 cells were transfected with pIRES-puro2 or pIRES-puro2-MUC1-C and selected in the presence of 400 ng/ml puromycin.

Quantitative real-time PCR. Total RNA was extracted from cells with TRIzol™ reagent (Invitrogen, Carlsbad, Calif.) and reverse transcribed with oligo(dT) priming and Superscript™ III reverse transcriptase (Invitrogen, Carlsbad, Calif.). Quantification of galectin-3 transcripts was performed with primer pairs CAACCAGTACTTGTATTTTGAATG (SEQ ID NO:16) and CAATGAGAACAACAGGAGAGTCA (SEQ ID NO:17) using Power SYBR™ Green QPCR Mastermix™ and ABI Prism™ 7000 sequence detections system (Applied Biosystems. Foster City, Calif.). Relative gene expression was determined using the comparative ddCT (threshold) method with GAPDH as the internal control.

Nuclear run-on assays. Nuclei were isolated from $5 \times 10^6$ cells and assayed as described (Patrone et al., 2000). In brief, run-on transcription was performed in the presence of biotin-16-UTP (Roche Applied Science) for 30 min at 30° C. RNA was purified using TRIzol reagent. The biotinylated RNA was isolated with Dynabeads M-280 (Invitrogen). Galectin-3 and, as an endogenous control, β-actin nascent transcripts were analyzed by quantitative RT-PCR. The difference in transcript level was calculated by the comparative $C_T$ method.

mRNA stability assays. Cells were treated with 1.3 µg/ml actinomycin D and harvested at different intervals. Total RNA was isolated and analyzed for galectin-3 and GAPDH mRNA levels by quantitative RT-PCT. The half life of galectin-3 mRNA was calculated using linear regression analysis.

Luciferase assays. Cells were transfected with pGL3-galectin-3 promoter constructs pGal-3(−3000/+141)-Luc or pGal-3(−836/+141)-Luc and pcDNA-LacZ using FuGENE™ 6 reagent (Roche Diagnostics, Indianapolis, Ind.). Galectin-3 promoter activity was measured 24 hours after transfection. To assess function of the galectin-3 3'UTR, cells were transfected with pMIR-Gal-3(3'UTR) and pMIR-β-galactosidase using FuGENE™ 6 reagent and assayed at 48 hours after transfection. Luciferase assays were performed with the luciferase assay system (Promega Corp., Madison, Wis.). The results were normalized to β-galactosidase activity and presented as relative luciferase activity.

Analysis of miR-322 expression. Northern blotting for detection of miRNAs was performed as described (Lee and Ambros, 2001; Johnson et al., 2005). Total cellular RNA (40 µg) isolated using TRIzol™ reagent (Invitrogen, Carlsbad, Calif.) was size fractionated in 15% urea-acrylamide gels. The RNA was transferred to positively charged nylon membranes (BrightStar™-Plus, Ambion, Austin, Tex.) by electroblotting. After UV-crosslinking and prehybridization, the RNA was hybridized to $^{32}$P-labeled probes against miR-322 (GCAGCGCCTCACGTTT) (SEQ ID NO:18) and U6-snRNA (GCGTGTCATCCTTGCGCAG) (SEQ ID NO:19) (Starfire™ Labeling System; Integrated DNA Technologies, Coralville, Iowa).

Antisense inhibition of miR-322. An antisense 2'-O-methyl oligoribonucleotide (GGUAUAGCAGCGCCUCACGUUUUG) (SEQ ID NO:20) against miR-322 and a scrambled 2'-O-methyl oligoribonucleotide (CACGGAUCUAGGUCGUAACGUAGG) (SEQ ID NO:21) (Integrated DNA Technologies) were transfected into BT549 cells (50 pmol/10,000 cells) in the presence of Lipofectamine™ 2000. At 72 hours after transfection, the cells were analyzed for galectin-3 expression.

Protein purification. CHO-K1 cells expressing hFc-MUC1-C/ED were adapted to grow as a suspension culture in mAb production medium (BD Biosciences, San Jose, Calif.) using the Cell Line 1000 chamber flask (Nunc, Rochester, N.Y.). The secreted hFc-MUC1-C/ED protein was purified using a protein-A column (Pierce Biotechnology, Rockford, Ill.). The galectin-3 proteins were purified from E. coli using an Asialofetulin column as described (Pelletier and Sato, 2002).

Identification of MUC1-C/ED cell surface binding proteins. Purified hFc-MUC1-C/ED and hFc (US Biologicals) were cross-linked to agarose beads. ZR-75-1 cells were grown in 0.1% FBS for 48 hours and washed with salt solution (10 mM MES, pH 6.2, 750 mM NaCl, 2 mM EDTA). The salt extract was passed through a 0.45 µm filter, diluted 3× in water, adjusted to 1 mM $CaCl_2$/3 mM MgCl2 (pH 7.4) and passed through a tandem hFc-MUC1-C/ED and control hFc column. The column was washed with 10 mM Tris-HCl, pH 7.4, 250 mM NaCl, 1 mM $CaCl_2$ and 3 mM $MgCl_2$, and eluted with 2 M NaCl and 5 mM EDTA. The eluate was dialyzed against PBS, concentrated, and analyzed by SDS-PAGE and silver staining.

Surface plasmon resonance analysis. Surface plasmon resonance measurements were determined using a BIACORE™ 3000 instrument at 25° C. Galectin-3 and galectin-3(63-250) were covalently coupled to CM5 Biacore™ sensor chips (500-1000 RU) at 30 µg/ml using the Biacore™ Amine Coupling kit. hFc-MUC1-C/ED and hFc diluted in running buffer (50 mM Tris-HCl, pH 7.4, 150 mM NaCl, 0.005% NP-40) were injected across galectin-3, galectin-3(63-250) or control flow cells at a rate of 30 µl/min. Regeneration of the sensor surface was performed with a 30-second pulse of 100 mM lactose. Association and dissociation kinetic constants were calculated by BIAevaluation™ software using 1:1 binding with a drifting base model.

In vitro deglycosylation. MUC1-C was immunoprecipitated from cell lysates, eluted from the beads with 50 mM glycine-HCl, pH 2.6, dialyzed against 50 mM sodium phosphate buffer, pH 7.0, and deglycosylated under denaturing conditions using the Glycokit™ glycosylation analysis kit (ProZyme, San Leandro, Calif.).

Immunofluorescence microscopy. Cells were fixed in 3.7% formaldehyde, permeabilized in 0.2% Triton™ X-100 and post-fixed in 3.7% formaldehyde. The cells were blocked with 10% normal goat serum and stained with antibodies specific for MUC1-N (MAb DF3) and antibodies specific for EGFR (Santa Cruz Biotechnology, Santa Cruz, Calif.), followed by fluorescein-conjugated antibodies specific for rabbit IgG or Texas Red-conjugated antibodies specific for mouse IgG (Jackson ImmunoResearch Laboratories, West Grove, Pa.). The cells were then mounted onto coverslips using slow-fade mounting reagent (Molecular Probes, Carlsbad, Calif.). Images were captured with a Zeiss LSM510 confocal microscope under 63× magnification and 1024× 1024 resolution.

Ectopic expression of pre-miR-322. Pre-miR constructs encoding mature miR-322 (AAACGUGAGGCGCUGCUAUA; SEQ ID NO:7) or a scrambled control sequence (GUCAGGUCAAACGGCCUAGAU; SEQ ID NO:8) were cloned into pcDNA 6.2-GW/miR vector (BLOCK-iT Pol II miR RNAi Expression Vector Kit; Invitrogen). The constructed clones were introduced into cells using Fugene6. The transfected cells were selected in 10 μg/ml blasticidin.

Example 2

MUC1 Upregulates Galectin-3 Expression in Carcinoma Cells

Figures 1B, 1C:
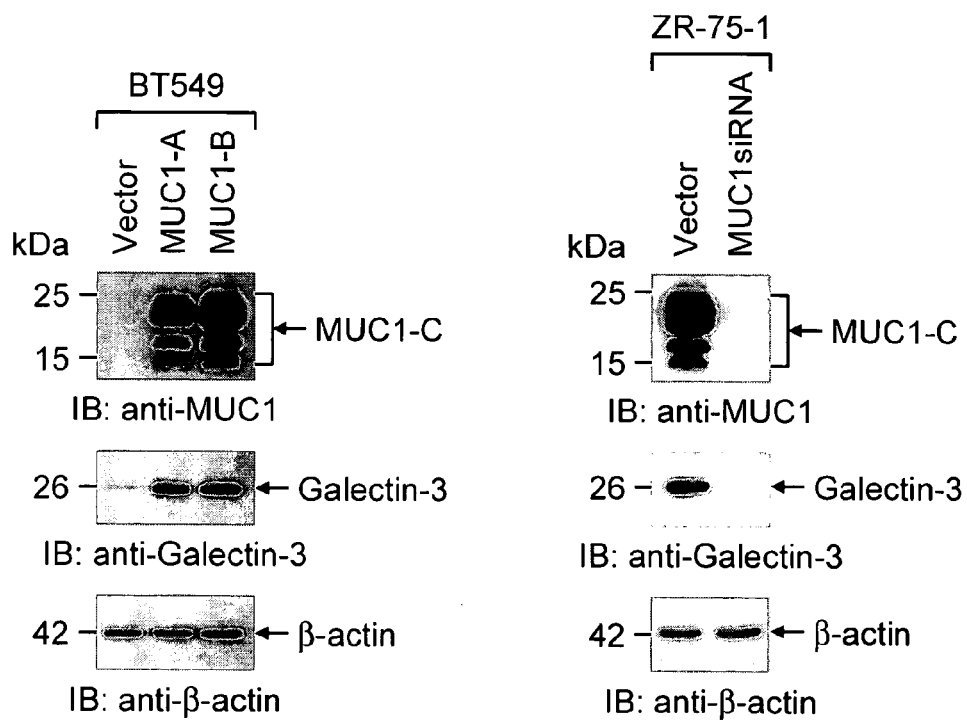

MUC1 and galectin-3 are both widely expressed in human carcinomas. To assess coexpression of MUC1 and galectin-3, lysates from diverse human carcinoma cells were analyzed. Cells expressing MUC1 were also positive for galectin-3 expression (FIG. 1A). The relationship between MUC1 and galectin-3 expression was further assessed in BT549 breast cancer cells, which are null for MUC1 and have low levels of galectin-3 (FIG. 1B). Stable expression of MUC1, but not the empty vector, was associated with substantial upregulation of galectin-3 (FIG. 1B). MUC1-dependent regulation of galectin-3 expression was also assessed in ZR-75-1 breast cancer cells that express endogenous MUC1 (Ren et al., 2004). Notably, stable silencing of MUC1 with a MUC1 siRNA (Ren et al., 2004) was associated with decreases in galectin-3 expression (FIG. 1C). Transient silencing of MUC1 with a pool of MUC1 siRNAs also resulted in downregulation of galectin-3 expression (FIG. 1D). Moreover, stable silencing of MUC1 in DU145 prostate cancer cells was associated with downregulation of galectin-3 (FIG. 1D). To exclude off-target effects of the MUC1 siRNA#2, which is directed against sequences encoding MUC1-C, we used MUC1siRNA#4. Silencing MUC1 with MUC1siRNA#4 similarly resulted in downregulation of galectin-3 expression (FIG. 1E). MUC1 siRNA#4 targets sequences in the MUC1-N coding region. Consequently, we transfected these cells to express MUC1-C (FIG. 1E). Notably, rescue of MUC1-C expression was associated with increases in galectin-3 (FIG. 1E). These findings indicate that MUC1-C upregulates galectin-3 expression.

These findings indicate that MUC1 upregulates galectin-3 expression.

Example 3

MUC1 Stabilizes Galectin-3 Transcripts

Figure 2A:
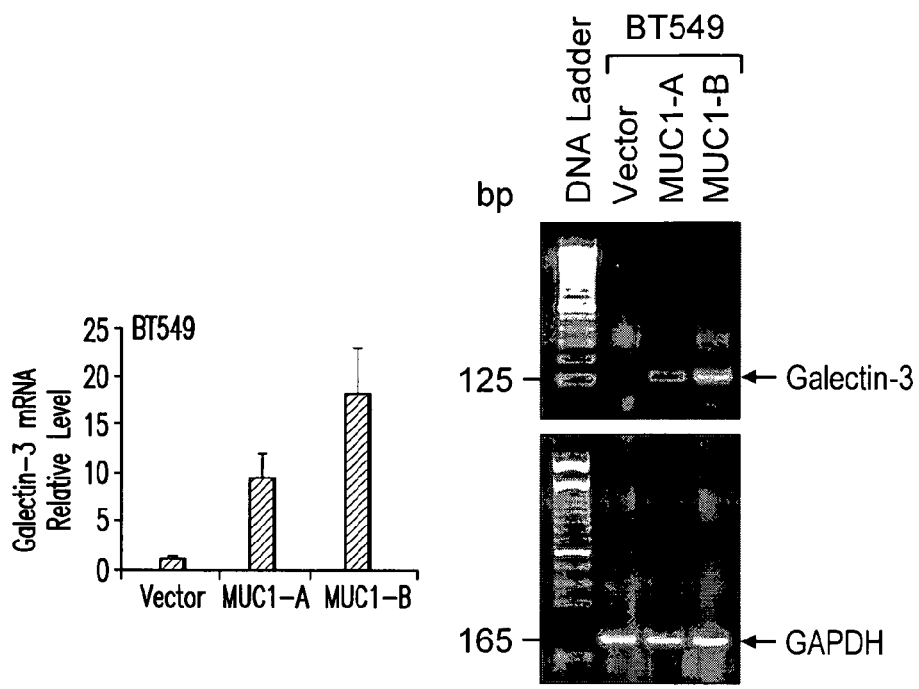
FIGS. 2A, 2B, 2C, 2D, 2E, 2F, 2G, 2H, 2I. MUC1 stabilizes galectin-3 transcripts. 2A, 2B—BT549/vector and BT549/MUC1 cells (A) or ZR-75-1/vector and ZR-75-1/MUC1siRNA (stably silenced for MUC1) cells (B) were analyzed for galectin-3 and GAPDH mRNA levels by semi-quantitative RT-PCR (left) and quantitative RT-PCR (right). The quantitative RT-PCR results (mean±SD from three replicates) are expressed as the relative galectin-3 mRNA levels (normalized to GAPDH) compared to that obtained with BT549/vector (A) and ZR-75-1/MUC1siRNA (B) cells (assigned a value of 1). 2C—DU145/CsiRNA and DU145/MUC1siRNA#4 cells were analyzed for galectin-3 and GAPDH mRNA levels by quantitative RT-PCR (left). DU145/MUC1 siRNA#4 cells were transfected with pIRES-puro2 or pIRES-puro2-MUC1-C and then analyzed by quantitative RT-PCR (right). The results (mean±SD from three replicates) are expressed as the relative galectin-3 mRNA levels (normalized to GAPDH) compared to that obtained with DU145/MUC1siRNA#4 (left) and DU145/MUC1siRNA#4 transfected with pIRES-puro2 (right) cells (assigned a value of 1). The asterisk (*) denotes a significant difference at p<0.05 as compared to control. 2D—BT549/ vector and BT549/MUC1 cells were treated with actinomycin D and then harvested at the indicated times. RNA was analyzed for galectin-3 and GAPDH mRNA levels by quantitative RT-PCR. The results are expressed as relative galectin-3 mRNA levels for BT549/vector (O) and BT549/MUC1 (□) cells. 2E—Construction of the galectin-3 3'UTR-luciferase reporter plasmid. BT549/vector and BT549/MUC1 cells (left) or ZR-75-1/vector and ZR-75-1/MUC1siRNA cells (right) were transfected with the pMIR-Gal-3(3'UTR) and, as a control, pMIR-β-galactosidase plasmids. The cells were analyzed for luciferase and β-gal activities at 48 h after transfection. The results (mean±SD of three experiments) are expressed as the relative luciferase activity (normalized to β-gal) compared to that in BT549/vector (left) or ZR-75-1/MUC1siRNA (right) cells (assigned a value of 1). The asterisk (*) denotes a significant difference at $p<0.05$ as compared to control. 2F—The indicated BT549 cells were transfected with pGal-3 (−3000/+141)—Luc and pcDNA-LacZ plasmids. 2G, 2H—ZR-75-1/MUC1siRNA and ZR-75-1/vector cells were transfected with the indicated pGal-Luc constructs and pcDNA-LacZ. The cells were assayed for luciferase and β-gal activities at 24 h after transfection. The results (mean±SD from three experiments) are expressed as relative galectin-3 promoter activity compared to that obtained with the BT549/vector (2F) or ZR-75-1/MUC1siRNA (2G and 2H) cells (assigned a value of 1). 2I—Galectin-3 gene transcription was assayed for the indicated BT549 (left) and ZR-75-1 (right) cells in run-on assays using the β-actin gene as an internal control. The results (mean±SD from three replicates) are expressed as the relative change in the abundance of newly transcribed galectin-3 mRNA.
Figure 2B:
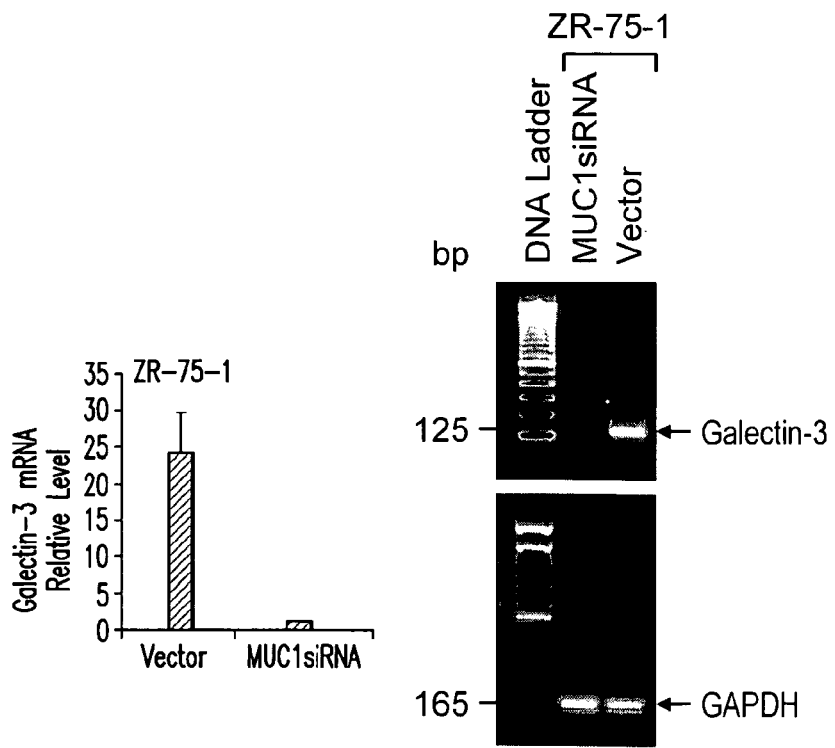
Figure 2C:
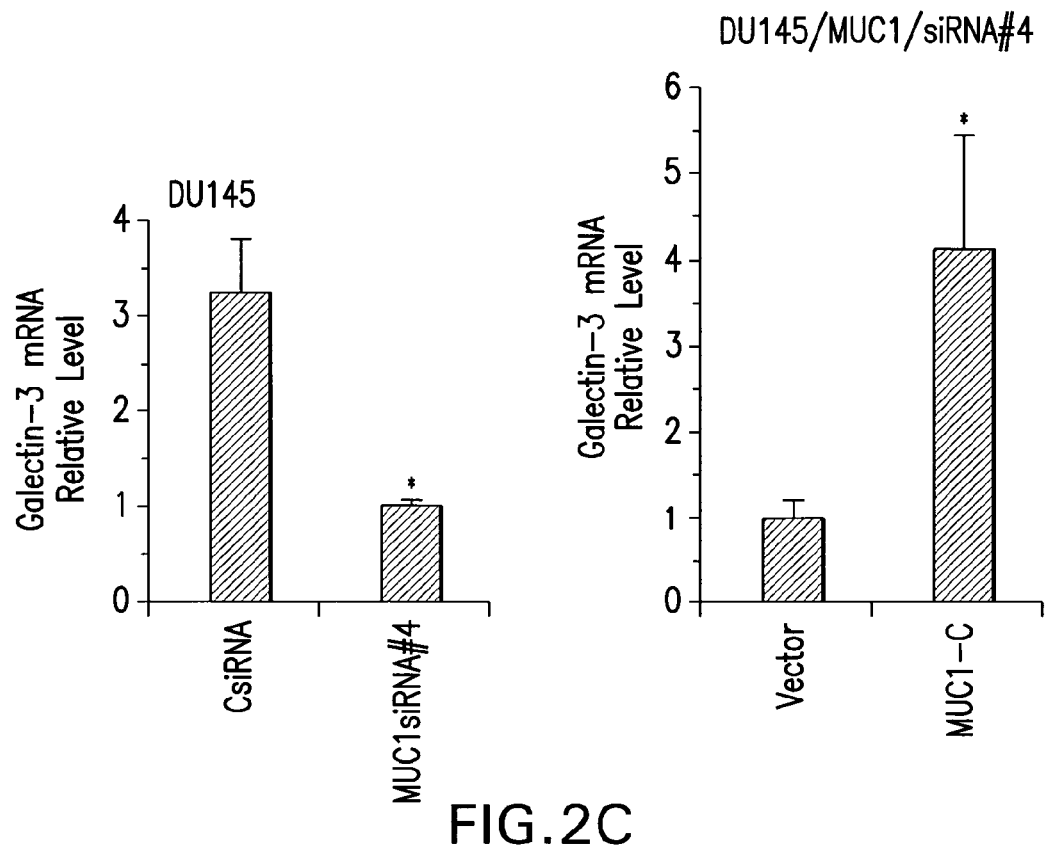
Figure 2D:
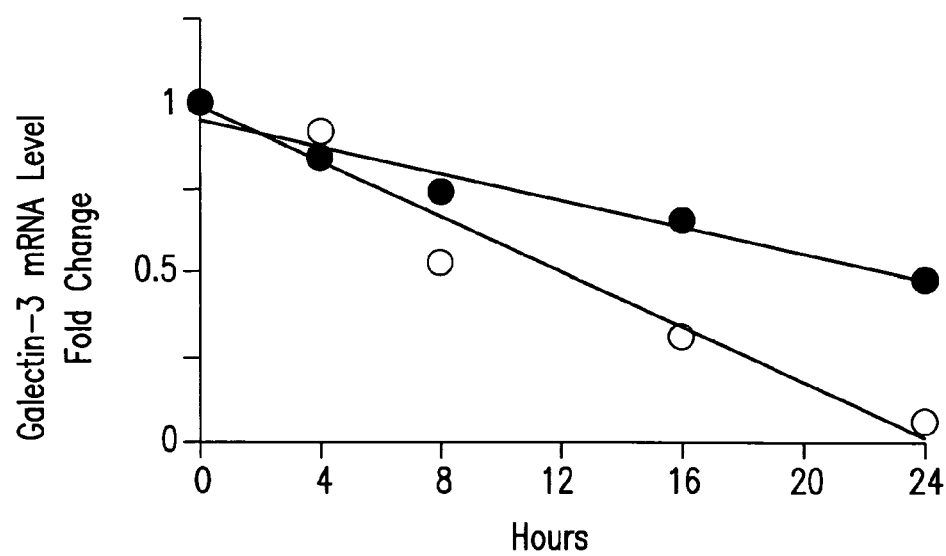
Figure 2E:
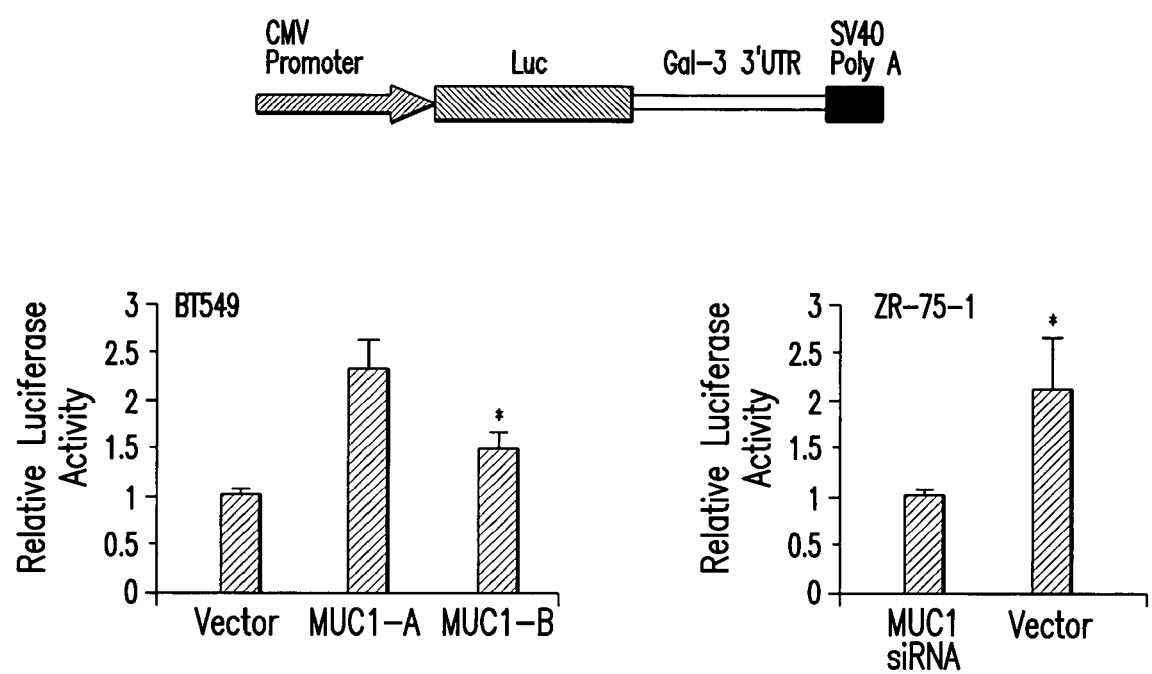
Figure 2F:
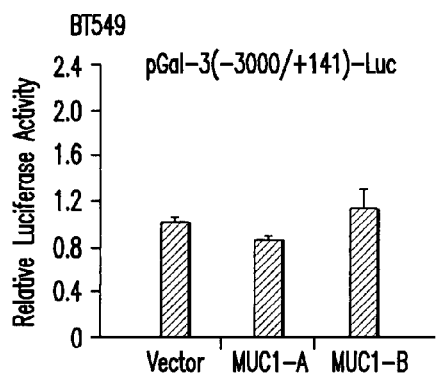
Figure 2G:
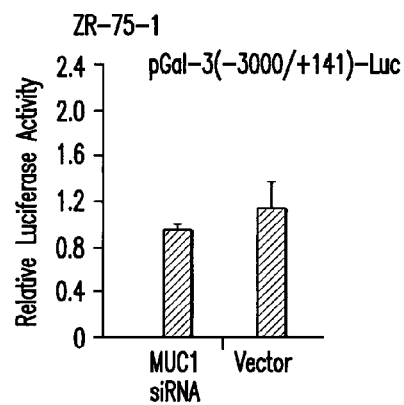
Figure 2H:
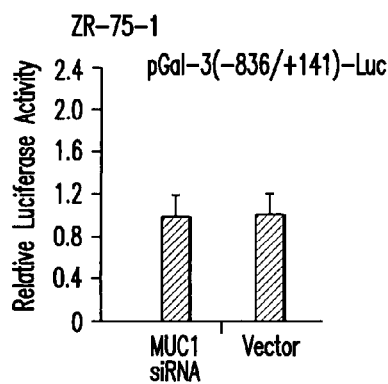
Figure 2I:
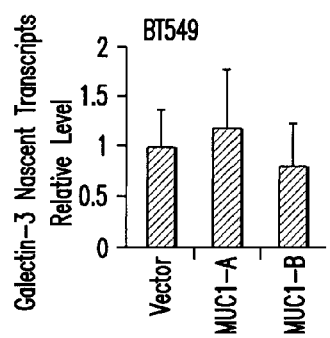
Figure 2I:
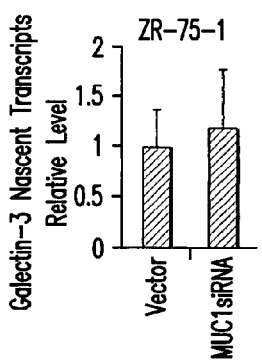

To define how MUC1 regulates galectin-3 expression, semi-quantitative RT-PCR analysis of galectin-3 mRNA levels was performed. BT549 cells stably expressing MUC1 exhibited increases in galectin-3 transcripts as compared to that in BT549/vector cells (FIG. 2A, left). MUC1-dependent upregulation of galectin-3 mRNA levels in BT549 cells was confirmed by quantitative RT-PCR (FIG. 2A, right). In concert with these results, stable silencing of MUC1 in ZR-75-1 cells decreased galectin-3 mRNA levels as determined by semi-quantative (FIG. 2B, left) and quantitative (FIG. 2B, right) RT-PCR. Stable silencing of MUC1 in DU145 cells also decreased galectin-3 mRNA levels (FIG. 2C, left). Moreover, expression of MUC1-C in DU145/MUC1 siRNA#4 cells was associated with increases in galectin-3 transcripts (FIG. 2C, right). To determine whether MUC1 activates galectin-3 gene transcription, regions (−3000 to +141 and −836 to +141) of the galectin-3 promoter were ligated upstream to a luciferase (Luc) reporter. The results obtained from transfecting pGal-3(−3000/+141)-Luc into BT549/vector and BT549/MUC1 cells indicated that MUC1 has little if any effect on activation of the galectin-3 promoter (FIG. 2F). MUC1 also had no apparent effect on activation of the pGal-3(−3000/+141)-Luc or pGal-3(−836/+141)-Luc constructs in ZR-75-1 cells (FIGS. 2G and 2H), indicating that MUC1 upregulates galectin-3 mRNA levels by a post-transcriptional mechanism. To extend this analysis to the endogenous galectin-3 gene, nuclear run-on assays were performed. The rate of galectin-3 gene transcription in BT549 cells was unaffected by stable expression of MUC1 (FIG. 21, left). In addition, silencing of MUC1 in ZR-75-1 cells had little if any effect on transcription of the galectin-3 gene (FIG. 21, right). These findings indicate that MUC1 increases galectin-3 mRNA levels by a posttranscriptional mechanism. To define the mechanism by which MUC1 increases galectin-3 mRNA levels, the stability of galectin-3 transcripts in BT549/vector and BT549/MUC1 cells was analyzed. Galectin-3 and GAPDH mRNA levels were assayed by quantitative RT-PCR after inhibiting transcription with actinomycin D. The rate of galectin-3 mRNA degradation in BT549/vector cells was increased as compared to that in BT549/MUC1 cells, indicating that MUC1 stabilizes galectin-3 transcripts (FIG. 2D). In this regard, the half-lives of galectin-3 transcripts were 22.8 and 12.0 h in the presence and absence of MUC1, respectively. To determine if the galectin-3 mRNA 3' untranslated region (3'UTR) is regulated by MUC1, the 3'UTR was ligated downstream to the luciferase gene in the pMIR reporter plasmid (FIG. 2E). Transfection of BT549 cells with pMIR-Gal-3(3'UTR) demonstrated that MUC1 increases expression of the luciferase reporter (FIG. 2E, left). Expression of pMIR-Gal-3(3'UTR) was also increased in ZR-75-1 cells by a MUC1-dependent mechanism (FIG. 2E, right). These findings indicate that MUC1 stabilizes galectin-3 transcripts by a mechanism involving the 3'UTR.

Example 4

Figure 3A:
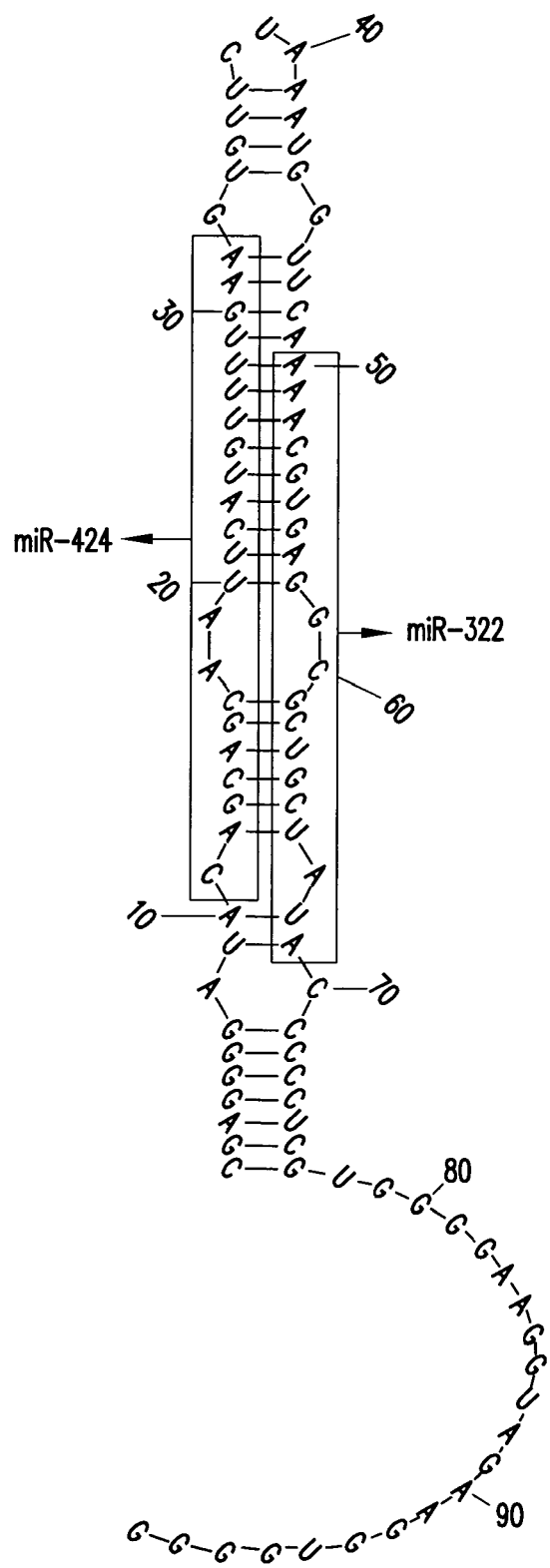
Figure 3B:
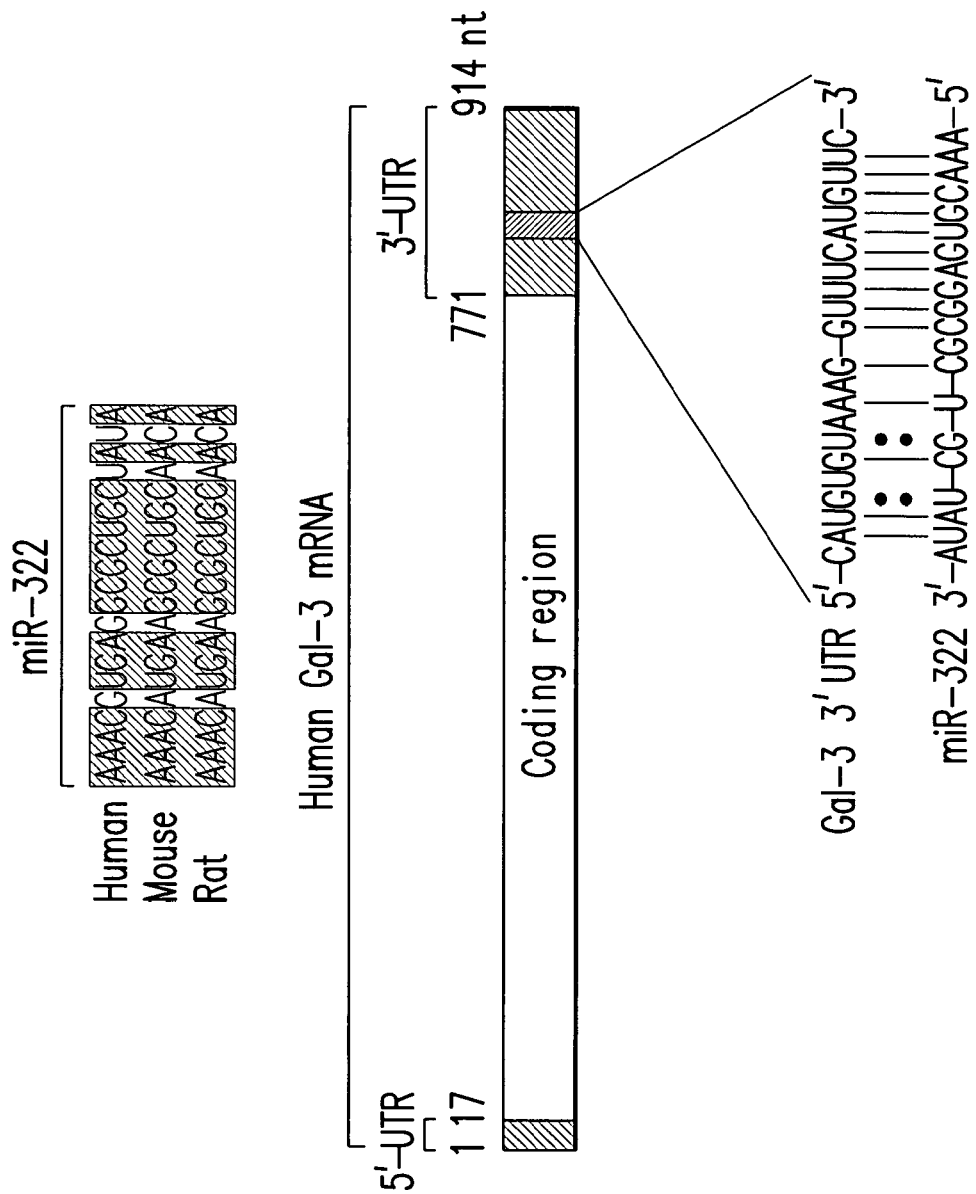
Figure 3C:
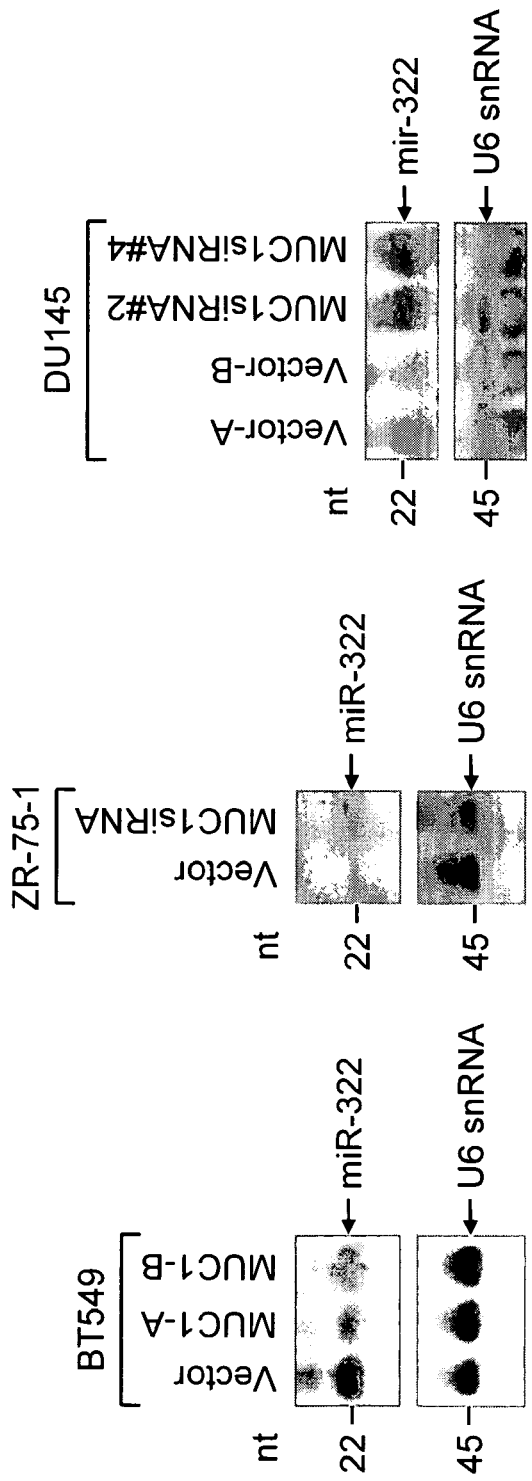
Figure 3F:
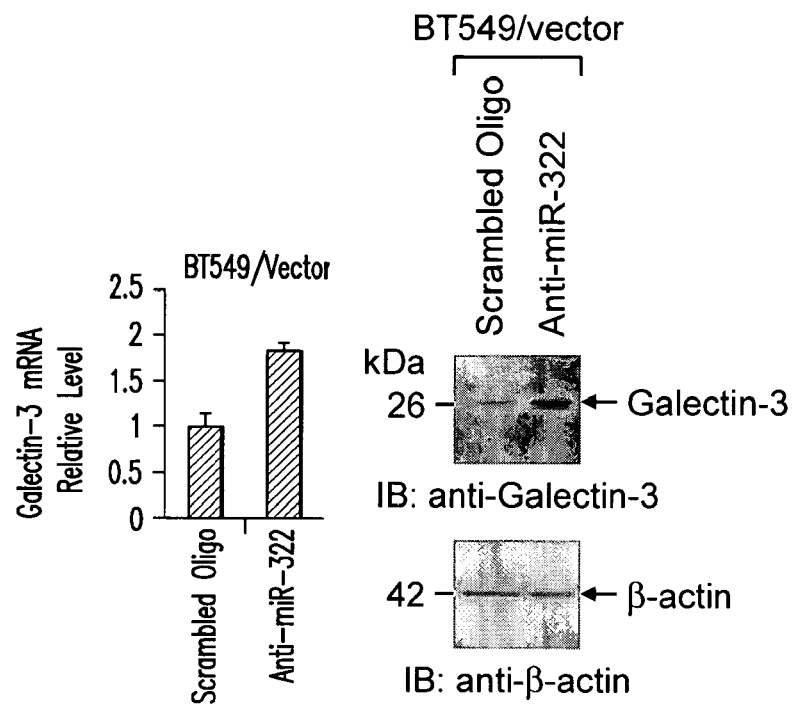
Figure 3G:
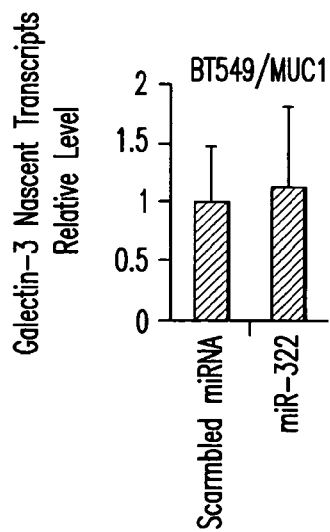

MUC1 Suppresses miR-322 Expression and Thereby Increases Stability of Galectin-3 mRNA The galectin-3 3'UTR has no identifiable AU-rich elements that function in the regulation of mRNA stability. Consequently, studies were conducted to determine if the galectin-3 3'UTR contains sequences that could be targeted by a microRNA. A search of the Sanger miRNA registry (http://microrna.sanger.ac.uk) identified miR-322 as a possible candidate. miR-322 is expressed from a stem-loop structure (pre-miR-322) at which miR-424 also originates (FIG. 3A). Expression of miR-424 has been demonstrated in human cells (Kasashima et al., 2004); however, there is no available evidence for a human miR-322. Alignment of mouse, rat and the putative human miR-322 revealed conservation of the sequences (FIG. 3B). In addition, human miR-322 has recognition sequences for the human galectin-3 3'UTR (FIG. 3B). Northern blot analysis of RNA from BT549/vector cells demonstrated expression of miR-322 (FIG. 3C, left). By contrast, it was found that miR-322 levels are decreased in BT549 cells that express MUC1 (FIG. 3C, left). Studies with ZR-75-1 cells further showed that miR-322 expression is suppressed by a MUC1-dependent mechanism (FIG. 3C, middle). Moreover, silencing MUC1 in DU145 cells with MUC1siRNA#2 or MUC1siRNA#4 increased miR-322 expression (FIG. 3C, right). These results thus demonstrate that MUC1 suppresses miR-322 expression. To determine whether miR-322 regulates galectin-3 expression, BT549/vector cells were transfected with an antisense 2'-O-methyl oligoribonucleotide targeted against miR-322 or, as a control, with a scrambled 2'-O-methyl oligoribonucleotide. It was found that anti-miR-322, and not the scrambled oligo, upregulates galectin-3 expression at the mRNA (FIG. 3F, left) and protein levels (FIG. 3F, right). Stability of galectin-3 transcripts was also determined by quantitative RT-PCR after actinomycin D treatment. Degradation of galectin-3 mRNA was increased in cells transfected with the scrambled oligo compared to that obtained with anti-miR-322 (FIG. 3D), indicating that miR-322 decreases galectin-3 mRNA stability. The half-lives of galectin-3 transcripts were 13.0 and 19.5 h in cells transfected with the scrambled oligo and anti-miR-322, respectively. As another approach, BT549/MUC1 cells were transfected with a pre-miR-322 or a scrambled miRNA. Ectopic miR-322 had no detectable effect on galectin-3 gene transcription as determined by run-on assays (FIG. 3G). Moreover, analysis of galectin-3 expression demonstrated that the ectopic miR-322 decreases galectin-3 mRNA and protein levels (FIG. 3E). These findings indicate that miR-322 decreases stability of galectin-3 transcripts.

Example 5

Direct Binding of the MUC1-C Extracellular Domain and Galectin-3

Figure 4A:
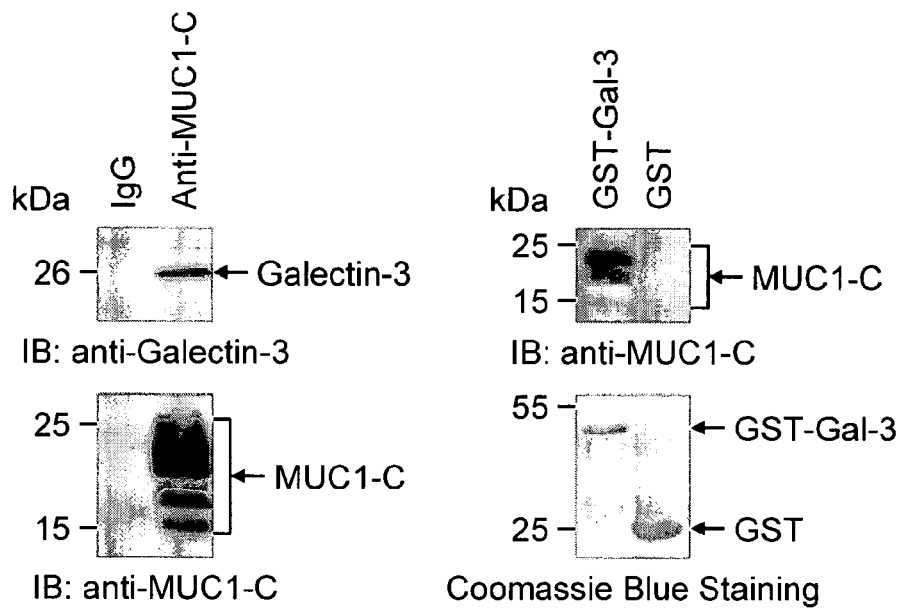
Figure 4B:
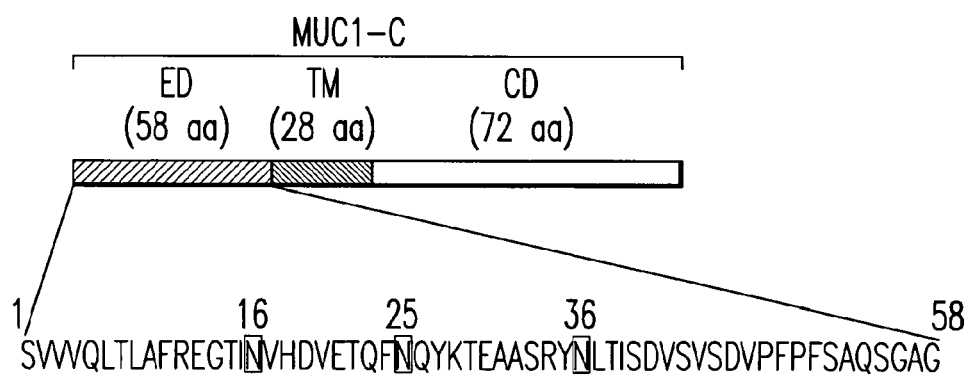
Figure 4E:
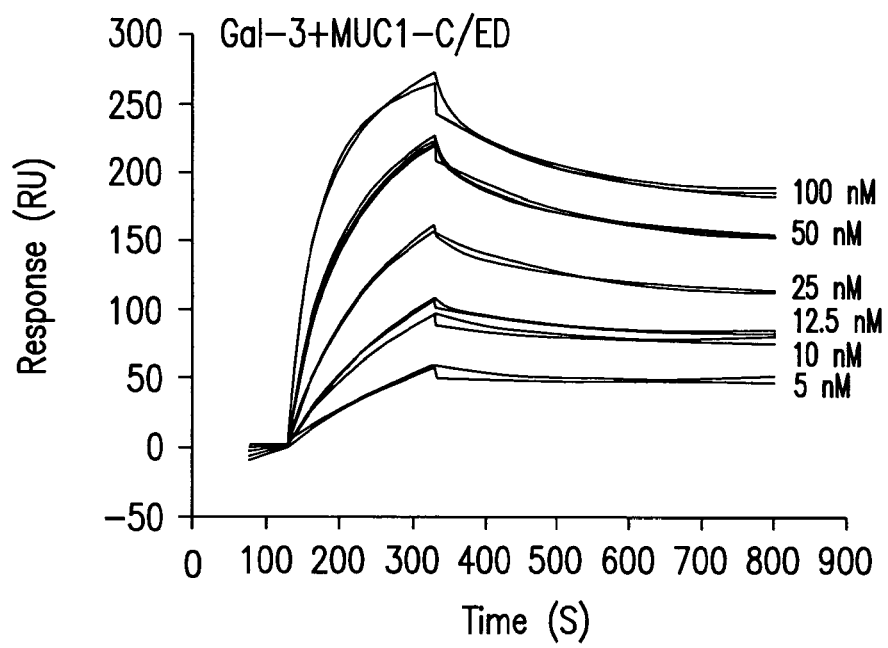
Figure 4F:
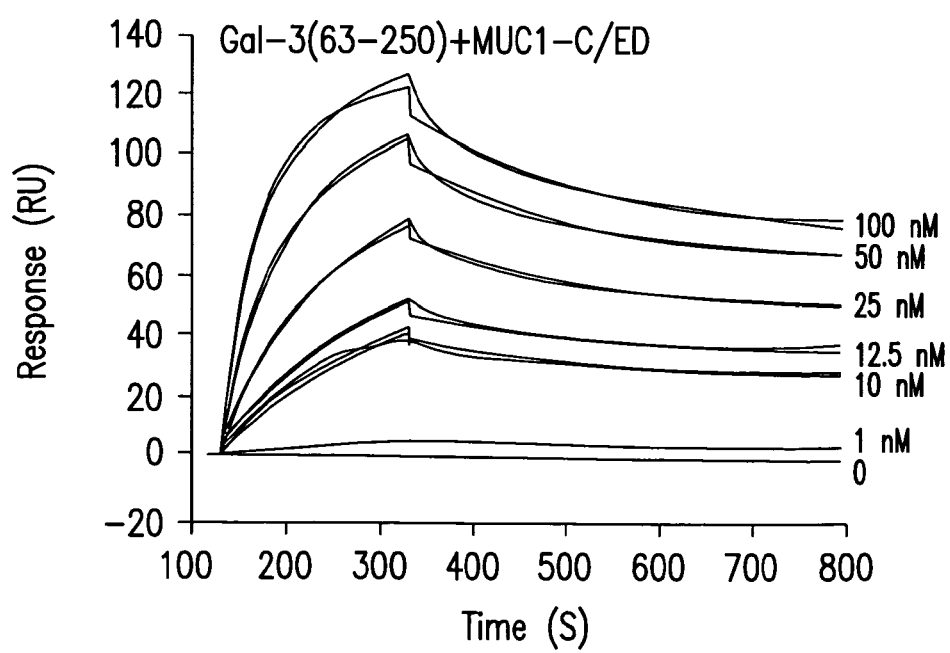

Galectin-3 binds to glycans on cell surface molecules like MUC1. To determine if the upregulation of galectin-3 expression is associated with binding of MUC1 and galectin-3, lysates from ZR-75-1 cells were immunoprecipitated with anti-MUC1-C or, as a control, IgG. Galectin-3 was detectable in the anti-MUC1-C, and not the IgG, precipitates (FIG. 4A, left). Incubation of a GST-galectin-3 fusion protein with ZR-75-1 cell lysates in pull-down experiments further demonstrated binding of MUC1-C and galectin-3 (FIG. 4A, right). MUC1-C consists of a 58 amino acid extracellular domain (ED), a 28 amino acid transmembrane domain (TM) and a 72 amino acid cytoplasmic domain (CD) (FIG. 4B). The MUC1-C extracellular domain (MUC1-C/ED) contains three potential N-glycosylation sites that could confer the interaction between MUC1-C and galectin-3 (FIG. 4B). To determine if galectin-3 associates with the MUC1-C/ED, the MUC1-C/ED was fused to human Fc (hFc-MUC1-C/ED) (FIG. 4B). hFc and hFc-MUC1-C/ED bound to agarose beads were incubated with supernatants from ZR-75-1 breast cancer cells. Analysis of adsorbed proteins by SDS-PAGE and silver staining demonstrated binding of a ~26 kDa protein to hFc-MUC1-C/ED and not hFc (FIG. 4C, left). Digestion of the adsorbed protein with trypsin and mass spectroscopy analysis of the tryptic peptides supported identity with galectin-J. Immunoblot analysis of the adsorbed protein also confirmed the association of MUC1-C/ED and galectin-3. To determine if MUC1-C/ED and galectin-3 interact directly, hFc or hFc-MUC1-C/ED were incubated with purified recombinant galectin-3. Analysis of the adsorbates by immunoblotting with anti-galectin-3 demonstrated binding of galectin-3 to hFc-MUC1-C/ED and not hFc (FIG. 4C, right). To define the region of galectin-3 that confers binding to MUC1-C/ED, GST fusion proteins with full-length galectin-3 or certain deletion mutants were prepared (FIG. 4D). MUC1-C/ED was pulled-down with GST-galectin-3 and GST-galectin-3(63-250) that contains the CRD (FIG. 4D). By contrast, there was no detectable binding of MUC1-C/ED and GST-galectin-3(1-62) or GST-galectin-3(1-138) that include the ND (FIG. 4D). The kinetics of the interaction between MUC1-C/ED and galectin-3 were assessed by immobilizing galectin-3 to a sensor chip and assaying for binding of MUC1-C/ED in a BIAcore (FIG. 4E). MUC1-C/ED bound to galectin-3 with a dissociation constant (KD) of 11.1 nM. Similar kinetics (KD=9.8 nM) were obtained for binding of MUC1-C/ED to galectin-3(63-250) (FIG. 4F). These findings indicate that MUC1-C/ED and galectin-3 bind directly and that this interaction is mediated by the galectin-3 CRD.

Example 6

MUC1-C Glycosylation is Necessary for the Galectin-3 Interaction

Figure 5C:
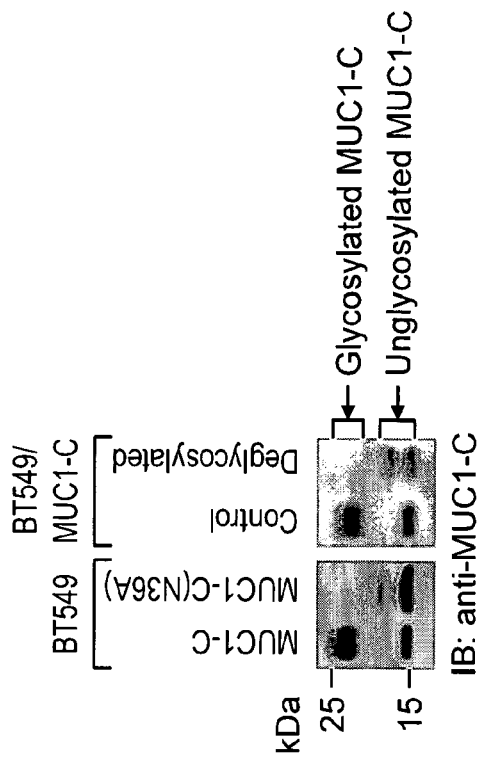
Figure 5D:
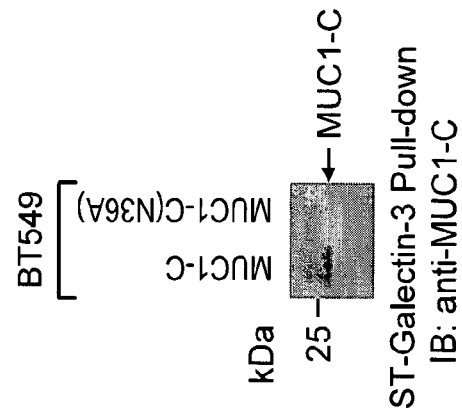
Figure 5A:
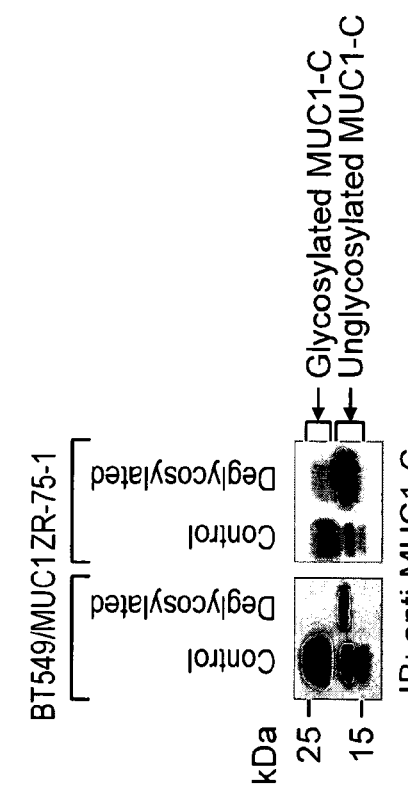
Figure 5B:
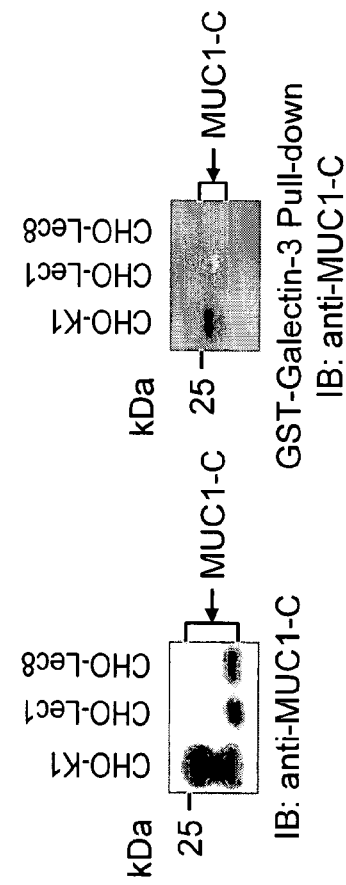

Galectin-3 binds to both β-galactoside-containing glycoproteins and non-glycosylated proteins (Shimura et al., 2004). MUC1-C is expressed as 25-20, 17 and 15 kDa species (FIG. 5A); however, it is not known if any of these species are subject to glycosylation. To assess MUC1-C glycosylation, anti-MUC1-C precipitates from BT549/MUC1 cells were incubated in the absence and presence of N-glycosidases. Deglycosylation was associated with a decrease in the broad anti-MUC1-C band at 25-20 kDa and an increase in the 17 kDa band (FIG. 5A, left), consistent with the presence of N-linked glycans. Similar results were obtained when endogenous MUC1-C from ZR-75-1 cells was incubated with N-glycosidases (FIG. 5A, right). To extend this analysis, MUC1-C was expressed in wild-type and glycosylation-deficient CHO cells. Expression of MUC1-C in CHO-Lec1 cells, which are deficient in N-glycosylation, was associated with loss of the 25-20 kDa band (FIG. 5B, left). A similar pattern of MUC1-C expression was observed in CHO-Lec8 cells, which are deficient for incorporation of β-galactosides (FIG. 5B, left). Notably, GST-galectin-3 pull-downs showed binding only to the 25-20 kDa MUC1-C expressed in CHO-K1 cells (FIG. 5B, right), consistent with interaction of galectin-3 and N-linked glycans on MUC1-C. The MUC1-C extracellular domain contains three asparagine residues (positions 16, 25 and 36; see FIG. 4B), one of which (NLT) conforms to a predicted N-glycosylation site. Consequently, wild-type MUC1-C or MUC1-C with a N36A mutation was stably expressed in human BT549 cells. Expression of wild-type MUC1-C was associated with anti-MUC1-C reactivity that was predominant at 25-20 and 15 kDa (FIG. 5C left). By contrast, expression of MUC1-C(N36A) resulted in anti-MUC1-C reactivity at 17 and 15 kDa (FIG. 5C, left), consistent with loss of the glycosylated 25-20 kDa species. As a control, deglycosylation of wild-type MUC1-C was also associated with reactivity at 17 and 15 kDa (FIG. 5C, right). Importantly, binding of galectin-3 was detectable with wild-type MUC1-C, but not with MUC1-C(N36A) (FIG. 5D). These findings indicate that galectin-3 binds to MUC1-C glycosylated at the Asn-36 site.

Example 7

MUC1-C Subunit Induces Galectin-3 Expression

Figure 6C:
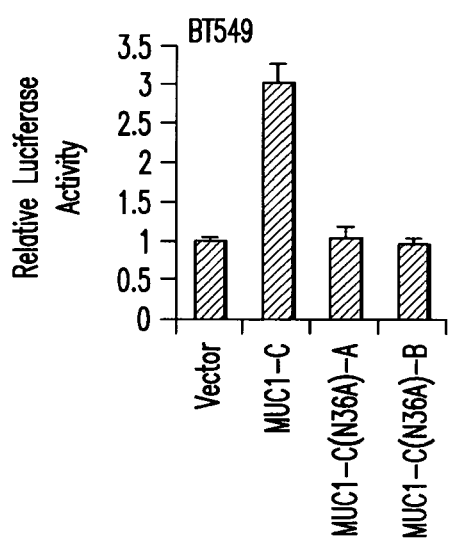
Figure 6D:
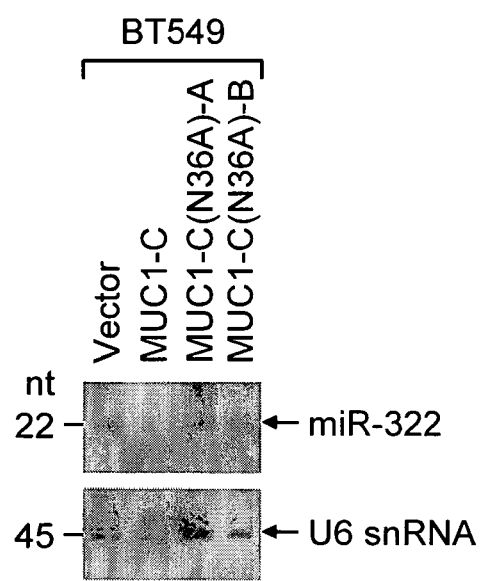

To further define the interaction between MUC1-C and galectin-3, BT549 cells stably transfected with MUC1-C or MUC1-C(N36A) were analyzed for induction of galectin-3 (FIG. 6A). The results demonstrate that MUC1-C is sufficient to upregulate galectin-3 expression (FIG. 6A). By contrast, MUC1-C(N36A) had little effect on galectin-3 levels (FIG. 6A). Semi-quantitative and quantitative RT-PCR also demonstrated that MUC1-C-induced upregulation of galectin-3 mRNA levels is substantially attenuated with MUC1-C (N36A) (FIG. 6B). As found with MUC1, there was no apparent effect of MUC1-C or MUC1-C(N36A) on activation of the galectin-3 promoter. However, MUC1-C, but not MUC1-C(N36A), was effective in increasing expression of the pMIR-Gal-3(3'UTR) reporter (FIG. 6C). In concert with these results, it was found that MUC1-C-induced suppression of miR-322 is also abrogated by the N36A mutation (FIG. 6D). These findings indicate that glycosylation of MUC1-C Asn-36 is necessary for suppression of miR-322 expression and upregulation of galectin-3.

Example 8

Galectin-3 Confers the Interaction Between MUC1 and Epidermal Growth Factor Receptor (EGFR)

Figure 5E:
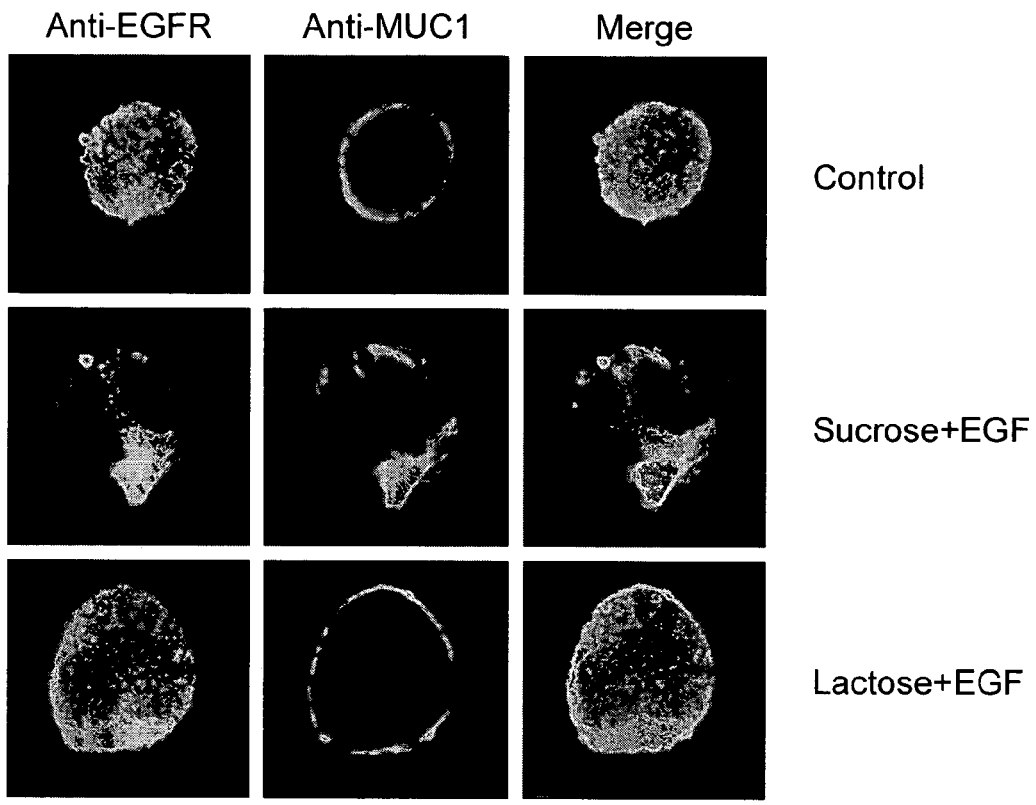
Figure 5F:
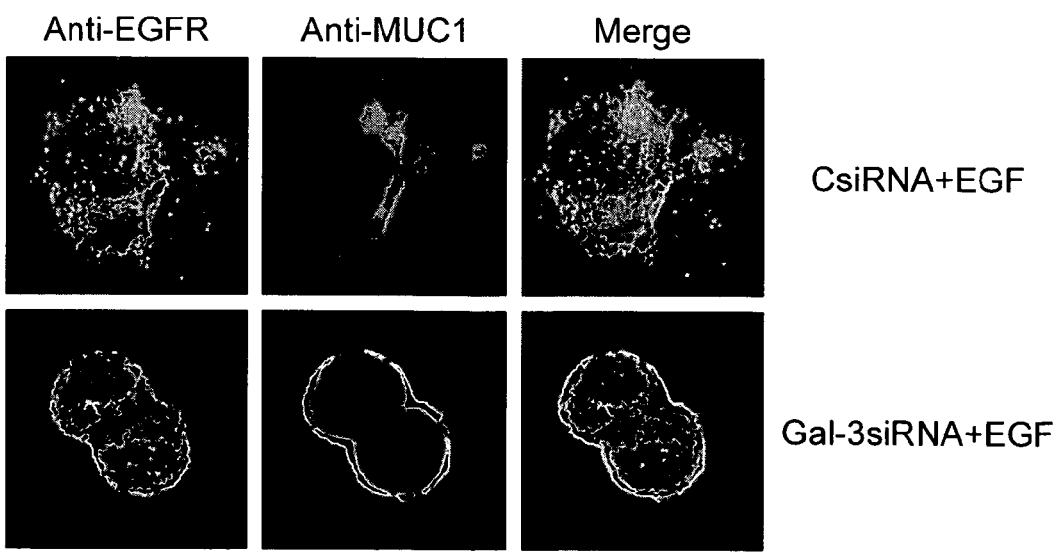
Figure 7A:
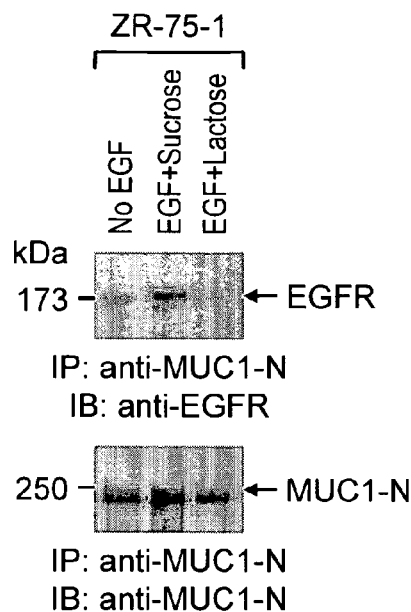
Figure 7B:
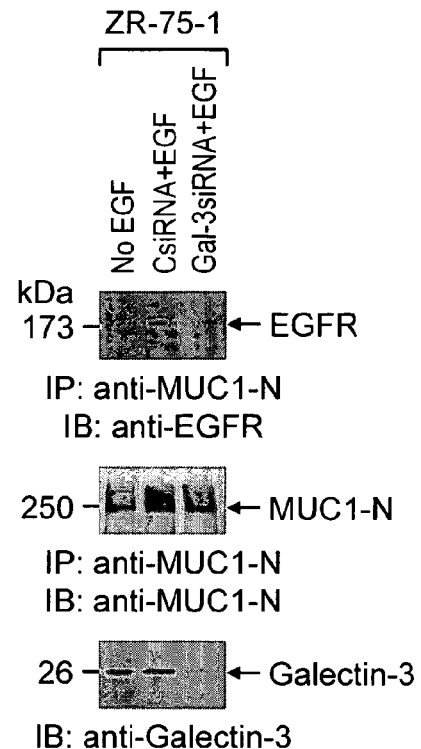
Figure 7C:
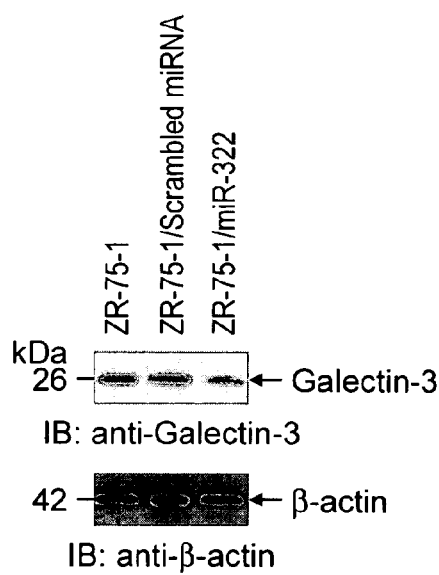
Figure 7D:
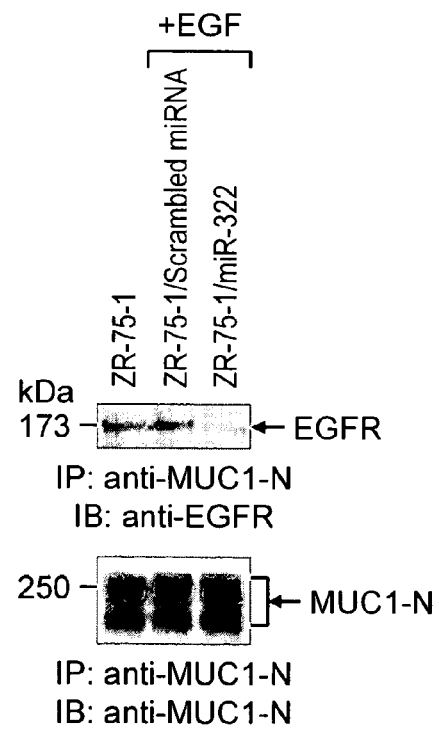

To determine if galectin-3 functions in the interaction between MUC1 and EGFR, ZR-75-1 cells were treated with lactose, a competitive inhibitor of galectin-3 binding and, as a control, with sucrose. EGF-stimulated binding of MUC1 and EGFR was attenuated by lactose and not sucrose, indicating that galectin-3 may facilitate this interaction (FIG. 7A). To extend the analysis, the ZR-75-1 cells were transfected with a pool of galectin-3 specific siRNAs or a control siRNA. The results demonstrate that silencing galectin-3 blocks the EGF-induced association of MUC1 and EGFR (FIG. 7B). To relate these studies to the downregulation of galectin-3 by miR-322, ZR-75-1 cells were transfected with pre-miR-322 or a scrambled miRNA. As found in BT549/MUC1 cells (FIG. 3E), ectopic miR-322 decreased galectin-3 expression (FIG. 7C). Moreover, downregulation of galectin-3 by ectopic miR-322 attenuated the EGF-induced interaction between MUC1 and EGFR (FIG. 7D). EGF stimulation is associated with increased colocalization of MUC1 and EGFR at the cell membrane (Li et al., 2001b). As shown previously by confocal microscopy (Li et al., 2001b), EGFR and MUC1 are uniformly distributed over the cell membrane of control ZR-75-1 cells (Supplemental FIG. 5E). Following EGF stimulation, EGFR and MUC1 cluster in patches (Li et al., 2001b). The colocalization of EGFR and MUC1 in clusters was blocked by lactose and not sucrose (FIG. 5E). Consistent with involvement of galectin-3, EGF-induced clustering of EGFR and MUC1 was also blocked by silencing galectin-3 (FIG. 5F). These findings indicate that MUC1 suppression of miR-322 and thereby upregulation of galectin-3 is of importance to the interaction between MUC1 and EGFR.

All of the compositions and/or methods disclosed and claimed herein can be made and executed without undue experimentation in light of the present disclosure. While the compositions and methods of this invention have been described in terms of some embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Pursuant to 37 C.F.R. 1.821(c), a sequence listing is submitted herewith as an ASCII compliant text file named "GENU019USST25", created on Oct. 15, 2012 and having a size of ~9 kilobytes. The content of the aforementioned file is hereby incorporated by reference in its entirety.

REFERENCES

The following references, to the extent that they provide exemplary procedural or other details supplementary to those set forth herein, are specifically incorporated herein by reference.

U.S. Pat. No. 4,642,334
U.S. Pat. No. 4,816,567
U.S. Pat. No. 4,918,166
U.S. Pat. No. 5,225,539
U.S. Pat. No. 5,565,334
U.S. Pat. No. 5,597,457
U.S. Pat. No. 5,790,421
U.S. Pat. No. 5,827,516
U.S. Pat. No. 5,874,415
U.S. Pat. No. 6,093,573
U.S. patent Ser. No. 10/486,278
Ahmad et al., Glycobiology, 14:817-825, 2004.
Akahani et al., Cancer Res., 57:5272-5276, 1997.
Aruffo et al., Cell, 61:1303-1313, 1990.
Ausubel et al., Current Protocols in Molecular Biology, Green Publish. Assoc. and Wiley Interscience, NY, 1989.
Bagga et al., Cell, 122:553-63, 2005.
Barrios et al., Eur. J. Immunol., 22:1365-1372, 1992.
Bartel, Cell, 116:281-97, 2004.
Beidler et al., J. Immunol., 141, 4053-60, 1988.
Better et al., Science, 240:1041-43, 1988.
Brody et al., Rev. Molecul. Biotech., 74:5-13, 2000.
Broughton, Curr. Opin. Chem. Biol., 1:392-398, 1997.
Califice et al. Int. J. Oncol., 25:983,992, 2004.
Chijiwa et al., J. Biol. Chem., 264:4924-7, 1989.
Cogoni and Masino, Nature, 399:166-169, 1999.
Cogoni et al., EMBO J., 15:3153-3163, 1996.
Cohen et al., J. Med. Chem., 33: 883-894, 1990.
Cristiano et al., J. Mol. Med., 73:479, 1995.
Dudas et al., Gastroenterology, 123:817-826, 2002.
European Patent Appln. 125,023
European Patent Appln. 171,496
European Patent Appln. 173,494
European Patent Appln. 184,187
Fire et al., Nature, 391:806-811, 1998.
Gendler et al., J. Biol. Chem., 263:12820-12823, 1988.
Gronenborn et al., Anal. Chem., 62(1):2-15, 1990.
Huang et al., Cancer Biol. Ther., 2:702-706, 2003.
Huang et al., Cancer Res., 65:10413-10422, 2005.
Hudson et al., J. Immunol. Methods, 23(1-2):177-189, 1999.
Hughes, Biochim. Biophys. Acta., 1473:172-185, 1999.
Huston et al., Hum. Antibodies, 10(3-4):127-142, 2001.
Jackson, Seminars in Oncology 24:L164-172, 1997.
Johnson et al., Cell, 120:635-647, 2005.
Jones et al., J. Med. Chem., 39:904-917, 1996.
Jones et al., Nature, 321:552-25, 1986.
Kasashima et al., Biochem. Biophys. Res. Commun., 322:403-410, 2004.
Kennerdell and Carthew, Cell, 95:1017-1026, 1998.
Krutzfeldt et al., Nature, 438:685-9, 2005.
Kufe et al., Hybridoma, 3:223-232, 1984.
Lee and Ambros, Science, 294:862-864, 2001.
Levitin et al., J. Biol. Chem., 280:33374-33386, 2005,
Li et al., Cancer Biol. Ther., 2:187-193, 2003.
Li et al., J. Biol. Chem., 276:35239-35242, 2001a.
Li et al., J. Biol. Chem., 276:6061-6064, 2001b.
Li et al., Mol. Cancer Res., 1:765-775, 2003.
Li et al., Mol. Cell. Biol., 18:7216-7224, 1998.
Li et al., Oncogene, 22:6107-6110, 2003.
Ligtenberg et al., J. Biol. Chem., 267:6171-6177, 1992.
Lim et al., Nature, 433:769-73, 2005.
Lin et al., Oncogene, 21:8001-8010, 2002.
Liu and Rabinovich, Nat. Rev. Cancer, 5:29-41, 2005.
Liu et al., J. Immunol., 139:3521-26, 1987.
Macao et al., Nat. Struct. Mol. Biol., 13:71-76, 2006.
Mashhoon et al., J. Biol. Chem., 275:200052-60, 2000.
Matarrese et al., FEBS Lett., 473:311-315, 2000.

McPherson, *J. Biol. Chem.*, 251:6300-6306, 1976.
Meggio et al., *Eur. J. Biochem.*, 187:89-94, 1990.
Merlo et al., *Cancer Res.*, 49:6966-6971, 1989.
Misquitta and Paterson, *Proc. Natl. Acad. Sci. USA*, 96:1451-1456, 1999.
Morrison, *Science*, 229:1202-07, 1985.
Nangia-Makker et al., *Int. J. Oncol.*, 7:1079-1087, 1995.
National Institutes of Health, *Current Protocols In Immunology*, Coligan et al., 2.8, 2.10 Wiley Interscience, 1991.
Navia et al., *Curr. Opinions Struct. Biol.*, 2:202-210, 1992.
Nishibata et al., *J. Med. Chem.*, 36(20):2921-2928, 1985.
Nishimura et al., *Canc. Res.*, 47, 999-1005, 1987.
Ochieng, *Glycoconj. J.*, 19:527-535, 2004.
Oi et al., *BioTechniques*, 4:214, 1986.
Paron et al., *Biochem. Biophys. Res. Commun.*, 302:545-553, 2003.
Partridge et al., *Science*, 306:120-124, 2004.
Patrone et al., *Biotechniques*, 29(5):1012-1014, 1016-1017, 2000.
Patterson et al., *Glycoconj J.*, 19:499-506, 2004.
PCT Appln. PCT/US00/03745
PCT Appln. PCT/US00/14667
PCT Appln. PCT/US86/02269
PCT Appln. PCT/US99/11913
PCT Appln. PCT/US99/18441
PCT Appln. WO 86/01533
Pelletier and Sato, *J. Biol. Chem.*, 277:17663-17670, 2002.
Poljak, *Structure*, 2(12):1121-1123, 1994.
*Protein NMR Spectroscopy, Principles and Practice*, Cavanagh et al., Academic Press, San Diego, 1996
Raina et al., *J. Biol. Chem.*, 279:20607-20612, 2004.
Ren et al., *Cancer Cell*, 5:163-175, 2004.
Ren et al., *Oncogene*, 25:20-31, 2006.
Rena et al., *EMBO Rep.*, 5:60-65, 2004.
Romano and Masino, *Mol. Microbiol.*, 6:3343-3353, 1992.
Sambrook et al., In: *Molecular cloning: a laboratory manual*, $2^{nd}$ Ed., Cold Spring Harbor Laboratory Press, Cold Spring Harbor, N.Y., 1989.
Schroeder et al., *Oncogene*, 23:5739-5747, 2004.
Seetharaman et al., *J. Biol. Chem.*, 273:13047-13052, 1998.
Shaw et al., *J. Natl. Cancer Inst.*, 80:1553-59, 1988.
Shimura et al., *Cancer Res.*, 64:6363-6367, 2004.
Siddiqui et al., *Proc. Natl. Acad. Sci. USA*, 85:2320-2323, 1988.
Stocks, *Drug Discov. Today*, 9(22): 960-966, 2004.
Sun et al., *Proc. Natl. Acad. Sci. USA*, 84:214-18, 1987.
Takenaka et al., *Cancer Lett.*, 195:111-119, 2003.
Takenaka et al., *Glycoconj. J.*, 19:543-549, 2004a.
Takenaka et al., *Mol. Cell Biol.*, 24:4395-4406, 2004b.
van den Brule et al., *J. Glycoconj.*, 19:537-542, 2004.
Veroeyan et al., *Science*, 239:1534, 1988.
Walzel et al., *Cell Signal.*, 14:861-868, 2002.
Weber, *Advances in Protein Chemistry*, 41:1-36, 1991.
Wei et al., *Cancer Cell*, 7:167-178, 2005.
Wen et al., *J. Biol. Chem.*, 278:38029-38039, 2003.
Wheeler et al., *Mol. Ther.*, 8(3):355-366, 2003.
Wider, BioTechniques, 29:1278-1294, 2000.
Wood et al., *Nature*, 314:446-49, 1985.
Wu and Belasco, *Mol. Cell. Biol.*, 25:9198-208, 2005.
Wu et al., *Proc. Natl. Acad. Sci. USA*, 103:4034-9, 2006.
Yamamoto et al., *J. Biol. Chem.*, 272:12492-12494, 1997.
Yoshii et al., *J. Biol. Chem.*, 277:6852-6857, 2002.
Yu et al., *J. Biol. Chem.*, 277:15819-15827. 2002.
Zhang et al., *Arch. Immunol. Ther. Exp.*, 52:307-315, 2004.

The invention claimed is:

1. A method of inhibiting binding of MUC1-C to galectin-3 in a cancer cell that expresses MUC1-C, the method comprising:
   contacting the cancer cell with a peptide fragment that comprises the extracellular domain, of MUC1-C, wherein said peptide fragment inhibits binding of galectin-3 to the extracellular domain of MUC1-C.

2. The method of claim 1, wherein the peptide fragment is fused to an immunoglobulin Fc region.

* * * * *

UNITED STATES PATENT AND TRADEMARK OFFICE
CERTIFICATE OF CORRECTION

Page 1 of 1

PATENT NO.       : 8,420,591 B2
APPLICATION NO.  : 12/517762
DATED            : April 16, 2013
INVENTOR(S)      : Donald W. Kufe It is certified that error appears in the above-identified patent and that said Letters Patent is hereby corrected as shown below:

In the Specification

In column 1, lines 9-11, delete
"The government owns rights in the invention pursuant to grant CA97098 from the National Cancer Institute of the National Institutes of Health."
and insert
--This invention was made with government support under grant CA97098 awarded by the National Cancer Institute of the National Institutes of Health. The government has certain rights in the invention.-- therefor.

Signed and Sealed this
Twenty-fifth Day of June, 2013

Teresa Stanek Rea
*Acting Director of the United States Patent and Trademark Office*

UNITED STATES PATENT AND TRADEMARK OFFICE
CERTIFICATE OF CORRECTION

Page 1 of 1

PATENT NO. : 8,420,591 B2
APPLICATION NO. : 12/517762
DATED : April 16, 2013
INVENTOR(S) : Kufe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 743 days.

Signed and Sealed this
Eleventh Day of November, 2014

Michelle K. Lee
*Deputy Director of the United States Patent and Trademark Office*